ll(12) United States Patent
Pfleger et al.

(10) Patent No.: US 8,617,856 B2
(45) Date of Patent: Dec. 31, 2013

(54) FATTY ACID-PRODUCING HOSTS

(75) Inventors: Brian F. Pfleger, Madison, WI (US); Rebecca M. Lennen, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 274 days.

(21) Appl. No.: 12/984,343

(22) Filed: Jan. 4, 2011

(65) Prior Publication Data
US 2011/0165637 A1 Jul. 7, 2011

Related U.S. Application Data

(60) Provisional application No. 61/292,918, filed on Jan. 7, 2010.

(51) Int. Cl.
*C12P 7/64* (2006.01)
(52) U.S. Cl.
USPC ......................................................... 435/134
(58) Field of Classification Search
USPC ......................................................... 435/134
See application file for complete search history.

(56) References Cited

U.S. PATENT DOCUMENTS

| | | | |
|---|---|---|---|
| 4,837,148 A | 6/1989 | Cregg | |
| 4,929,555 A | 5/1990 | Cregg et al. | |
| 5,000,000 A | 3/1991 | Ingram et al. | |
| 5,028,539 A | 7/1991 | Ingram et al. | |
| 5,077,214 A | 12/1991 | Guarino et al. | |
| 5,424,202 A | 6/1995 | Ingram et al. | |
| 5,482,846 A | 1/1996 | Ingram et al. | |
| 5,602,030 A | 2/1997 | Ingrahm et al. | |
| 5,679,543 A | 10/1997 | Lawliss | |
| 2007/0244343 A1 | 10/2007 | Brevoord et al. | |

FOREIGN PATENT DOCUMENTS

| EP | 0 238 023 A2 | 9/1987 |
|---|---|---|
| WO | WO 96/00787 A1 | 1/1996 |
| WO | WO 2007/136762 A2 | 11/2007 |

OTHER PUBLICATIONS

Lu et al. Metabolic Engineering 10(2008): 333-339.*
Alper et al., 2005, Tuning genetic control through promoter engineering, *PNAS*, 102(36):12678-83.
Antoine et al., 1992, Isolation and molecular characterization of a novel broad-host-range plasmid from *Bordetella bronchoseptica* with sequence similarities to plasmids from Gram-positive organisms, *Mol. Microbiol.*, 6:1785-1799.
Bannerjee et al., 2002, *Botryococcus braunli*: A Renewable Source of Hydrocarbons and Other Chemicals, *Critical Reviews in Biotechnology*, 22:245-279.
Beach et al., 1982, Functionally homologous cell cycle control genes in budding and fission yeast, *Nature*, 300:706.
Becker et al., High-Efficiency Transformation of Yeast by Electroporation, In: Guide to Yeast Genetics and Molecular Biology,
Methods in Enzymology, 194:182-187, Abelson, J.N. and Simon, M.I., editors, Academic Press, Inc., New York, (1991).
Benoist et al., 1981, In vivo sequence requirements of the SV40 early promoter region, *Nature*, (London) 290:304.
Bitter et al., 1987, Expression and Secretion Vectors for Yeast, *Methods in Enzymology*, 153:516-544.
Black et al., 2003, Transmembrane Movement of Exogenous Long-Chain Fatty Acids: Proteins, Enzymes, and Vectorial Esterification, *Microbiol. Mol. Biol. Rev.*, 67:454-472.
Bligh et al., 1959, A Rapid Method of Total Lipid Extraction and Purification, *Can. J. Biochem. Physiol.*, 37:911-917.
Camilli et al., 2006, Bacterial Small-Molecule Signaling Pathways, *Science*, 311:1113.
Chang et al., 1978, Construction and Characterization of Amplifiable Multicopy DNA Cloning Vehicles Derived from the P15A Cryptic Miniplasmid, *J. Bacteriol.*, 134:1141-1156.
Chang et al., 1979, High Frequency Transformation of *Bacillus subtilis* Protoplasts by Plasmid DNA, *Molecular General Genetics*, 168:111-115.
Cregg et al., 1985, *Pichia pastoris* as a Host Systems for Transformations, *Mol. Cell. Biol.*, 5:3376.
Cronan, 2006, A family of arabinose-inducible *Escherichia coli* expression vectors having pBT322 copy control, *Plasmid*, 55:152-157.
Das et al., 1984, Transformation of *Kluyveromyces fragilis*, *J. Bacteriol.*, 158:1165.
Datsenko et al., 2000, One-step inactivation f chromosomal genes in *Escherichia coli* K-12 using PCR products, *Proc. Natl. Acad. Sci. USA*, 97:6640-6645.
Davidow et al., 1985, Integrative transformation of the yeast *Yarrowia lipolytica*, *Curr. Genet.*, 10:380-471.
Davis et al., 2000 Overproduction of Acetyl-CoA Carboxylase Activity Increases the Rate of Fatty Acid Biosynthesis in *Escherichia coli*, *J. Biol. Chem.*, 275:28593-28598.
Davis et al., 2001, Inhibition of *Escherichia coli* Acetyl Coenzyme A Carboxylase by Acyl-Acyl Carrier Protein, *J. Bacteriol.*, 183:1499-1503.
De Lay et al., 2007, in Vivo Functional Analyses of the Type II Acyl Carrier Proteins of Fatty Acid Biosynthesis, *J. Biol. Chem.*, 282:20319-20328.
De Louvencourt et al., 1983, Transformation of *Kluyveromyces lactis* by Killer Plasmid DNA, *J. Bacteriol.* 154:737.
Dubnau et al., 1971, Fate of Transforming DNA following uptake by Competent *Bacillus subtilis*, *Journal of Molecular Biology*, 56:209-221.
Eccleston et al., 1998, Expression of Lauroyl-Acyl Carrier Protein Thioesterase in *Brassica napus* Seeds Induces Pathways for Both Fatty Acid Oxidation and Biosynthesis and Implies a Set Point for Triacylglyceraol Accumulation, *Plant Cell*, 10:613-621.
Feng et al., 2009, *Escherichia coli* Unsaturated Fatty Acid Synthesis—Complex Transcription of the fabA Gene and In Vivo Identification of the Essential Reaction Catalyzed by FabB, *J. Biol. Chem.*, 284:29526-29535.

(Continued)

*Primary Examiner* — Tekchand Saidha
(74) *Attorney, Agent, or Firm* — Daniel A. Blasiole; Joseph T. Leone, Esq.; DeWitt Ross & Stevens SC

(57) ABSTRACT

Described are hosts for overproducing a fatty acid product such as a fatty acid. The hosts include an exogenous nucleic acid encoding a thioesterase and, optionally, an exogenous nucleic acid encoding an acetyl-CoA carboxylase, wherein an acyl-CoA synthetase in the hosts are functionally deleted. The hosts preferably include the nucleic acid encoding the thioesterase at an intermediate copy number. The hosts are preferably recombinantly stable and growth-competent at 37° C. Methods of producing a fatty acid product comprising culturing such hosts at 37° C. are also described.

25 Claims, 9 Drawing Sheets

(56) References Cited

OTHER PUBLICATIONS

Friehs, 2004, Plasmid Copy Number and Plasmid Stability, *Adv. Biochem. Eng. Biotechnol.*, 86:47-82.

Foecking et al., 1986, Powerful and versatile enhancer-promoter unit for mammalian expression vectors, *Gene*, 45:101.

Gaillardin et al., 1985, Integrative transformation of the yeast *Yarrowia lipolytica*, *Curr. Genet.*, 10:49.

Ganeva et al., 1994, Influence of glucose and other substrates on electric field and polyethylene glycol-mediated transformation of intact yeast cells, *FEMS Microbiology Letters*, 121:159-64.

Ghosh et al., 2007, Characterization and cloning of a stearoyl/oleoyl specific fatty acyl-acyl carrier protein thioesterase from the seeds of *Madhuca longifolia (latifolia)*, *Plant Physiol. Biochem.*, 45:887-897.

Gleeson et al., 1986, Transformation of the Methylotrophic Yeast *Hansenula polymorpha*, *J. Gen. Microbiol.*, 132:3459.

Glick, 1987, Factors affecting the expression of foreign proteins in *Escherichia coli*, *J. Ind. Microbiol.* 1:277.

Guzman et al., 1995, Tight Regulation, Modulation, and High-Level Expression by Vectors Containing the Arabinose $P_{BAD}$ Promoter, *J. Bacteriol.*, 177:4121-4130.

Hamer et al., 1982, Regulation in Vivo of a Cloned Mammalian Gene: Cadmium Induces the Transcription of a Mouse Metallothionein Gene in SV40 Vectors, *J. Mol. Appl. Gen.*, 1:273.

Hearn et al., 2009, Transmembrane passage of hydrophobic compounds through a protein channel wall *Nature*, 458:367-370.

Heath et al., 1996, Regulation of Fatty Acid Elongation and Initiation by Acyl-Acyl Carrier Protein in *Escherichia coli*, *J. Biol. Chem.* 271:1833-1836.

Hinnen et al., 1978, Transformation of yeast, *Proc. Natl. Acad. Sci.*, USA, 75:1929.

Ito et al., 1983, Transformation of Intact Cells Treated with Alkali Cations, *J. Bacteriol*, 153:163.

Janikowski et al., 2002, Use of a two-phase partitioning bioreactor for degrading polycyclic aromatic hydrocarbons by a *Sphingomonas* sp., *Appl. Microbiol. Biotechnol.*, 59:368-376.

Jha et al., 2006, Cloning and functional expression of an acyl-ACP thioesterase FatB type from *Diploknema (Madhuca) butyracea* seeds in *Escherichia coli*, *Plant Physiol. Biochem.*, 44:645-655.

Johnston et al., 1982, Isolation of the yeast regulatory gene GAL4 and analysis of it dosage effects on the galactose/melibiose regulon, *PNAS* (USA), 79:6971.

Jones et al., 2000, Low-Copy Plasmids can Perform as Well as or Better Than High-Copy Plasmids for Metabolic Engineering of Bacteria, *Metabolic Engineering*, 2:328-338.

Kalscheur et al., 2006, Microdiesel: *Escherichia coli* engineered for fuel production, *Microbiology*, 152:2529-36.

Koehler et al., 1987, *Bacillus subtilis (natto)* Plasmid pLS20 Mediates Interspecies Plasmid Transfer, *Journal of Bacteriology*, 169:5771-5278.

Kunze et al., 1985, Transformation of the industrially important yeasts *Candida maltosa* and *Pichia guilliermondii*, *J. Basic Microbiol.* 25:141.

Kurtz et al., 1986, Integrative Transformation of *Candida albicans*, Using a Cloned *Candida ADE2* Gene, *Mol. Cell. Biol.*, 6:142.

Li et al., 1993, Growth Rate Regulation of *Escherichia coli* Acetyl Coenzyme A Carboxylase, Which Catalyzes the First Committed Step of Lipid Biosynthesis, *J. Bacteriol.*, 175:332-340.

Lu et al., 2008, Kinetic Modeling Analysis of Maleic Acid-Catalyzed Hemicellulose Hydrolysis in Corn Stover, *Biotechnol. Bioeng.*, vol. 101; Issue 6: pp. 1170-1181.

Lynch et al., 2006, Broad Host Range Vectors for Stable Genomic Library Construction, *Biotechnol. Bioeng.*, 94:151-158.

Mäki-Arvela et al., Catalytic Deoxygenation of Fatty Acids and Their Derivatives, 2007, *Energy & Fuels*, 21:30-41.

Mäki-Arvela et al., 2008, Continuous decarboxylation of lauric acid over Pd/C catalyst, *Fuel*, 87(17-18):3543-3549.

Malardier et al., 1989, Cloning of the nitrate reductase gene (*NiaD*) of *Aspergillus nidulans* and its use for transformation of *Fusarium oxysporum*, *Gene*, 78:147-56.

Manivasakam et al., 1993, High efficiency transformation of *Saccharomyces cerevisiae* by electroporation, *Nucleic Acids Research*, 21(18):4414-5.

McKnight et al., 1982, Functional Relationships between Transcriptional Control Signals of the Thymidine Kinase Gene of Herpes Simplex Virus, *Cell*, 31:355.

Murli et al., 2000, A Role for the *umuDC* Gene Products of *Escherichia coli* in Increasing Resistance to DNA Damage in Stationary Phase by Inhibiting the Transition to Exponential Growth, *J. of Bact.*, 182:1127.

Newman et al., 2006, High-Level Production of Amorpha-4, 11-Diene in a Two-Phase Partitioning Bioreactor of Metabolically Engineered *Escherichia coli*, *Biotechnol. Bioeng.*, 95:684-691.

Nordström et al., 2006, Copy-Number control of the *Escherichia coli* chromosome: a plasmidologists' view, *EMBO Rep.*, 7:484-489.

Ohlrogge et al., 1995, Alteration of Acyl-Acyl Carrier Protein Pools and Acetyl-CoA Carboxylase Expression in *Escherichia coli* by a Plant Medium Chain Acyl-Acyl Carrier Protein Thioesterase, *Arch. Biochem. Biophys.*, 317:185-190.

Orlandi et al., 1989, Cloning immunoglobulin variable domains for expression by the polymerase chain reaction, *PNAS* (USA), 86:3833.

Overath et al., 1969, Fatty Acid Degradation in *Escherichia coli* An Inducible Acyl-CoA Synthetase, the Mapping of the *old*-Mutations, and the Isolation of Regulatory Mutants, *Eur. J. Biochem.*, 7:559-574.

Providenti et al., 2006, The copy-number of plasmids and other genetic elements can be determined by SYBR-Green-based quantitative real-time PCR, *J. Microbiol. Methods*, 65:476-487.

Reading et al., 2006, Quorum sensing: the many languages of bacteria, *FEMS Microbiol. Lett.*, 254:1-11.

Reeves et al., 1992, Multiple transformation of *Saccharomyces cerevisiae* by protoplast fusion, *FEMS Microbiology Letters*, 99:193-198.

Roggenkamp et al., 1986, Transformation of the methylotrophic yeast *Hansenula polymorpha* by autonomous replication and integration vectors, *Mol. Gen. Genet.*, 202:302.

Sambrook et al., 2001, in: *Molecular Cloning: A Laboratory Manual*, 3rd Ed., Cold Spring Harbor Laboratory Press.

Sardessai et al., 2002, Tolerance of bacteria to organic solvents, *Res. Microbiol.*, 153:263-268.

Schirmer et al., 2010, Microbial Biosynthesis of Alkanes, *Science*, 329(5991):559-62.

Serrano-Vega et al., Cloning, characterization and structural model of a FatA-type thioesterase from sunflower seeds (*Helianthus annuus* L.), 2005, *Planta*, 221:868-880.

Shigekawa et al., 1988, Electroporation of Eukaryotes and Prokaryotes: A General Approach to the Introduction of Macromolecules into Cells, *Biotechniques*, 6:742-751.

Silver et al., 1984, Amino terminus of the yeast *GAL4* gene product is sufficient for nuclear localization, *PNAS* (USA), 81:5951.

Sugiura et al., 1993, Minimal Essential Origin of Plasmid pSC101 Replication: Requirement of a Region Downstream of Iterons, *J. Bacteriol.*, 175(18):5993-6001.

Thomason et al., 2007, *E. coli* Genome Manipulation by P1 Transduction, *Curr. Protoc. Mol. Biol.*, 1:17.

Van Den Berg et al., 1990, *Kluyveromyces* As a Host for Heterologous Gene Expression: Expression and Secretion of Prochymosin, *Bio/Technology*, 8:135.

Venturi, 2006, Regulation of quorum sensing in *Pseudomonas*, *FEMS Microbiol. Rev.*, 30:274-291.

Voelker et al., 1992, Fatty Acid Biosynthesis Redirected to Medium Chains in Transgenic Oilseed Plants, *Science*, 257:72-74.

Voelker et al., 1994, Alteration of the Specificity and Regulation of fatty Acid Synthesis of *Escherichia coli* by Expression of a Plant Medium-Chain Acyl-Acyl Carrier Protein Thioesterase, *J. Bacteriol.*, 176:7320-7327.

Vorum et al., 1992, Solubility of long-chain fatty acids in phosphate buffer at pH 7.4, *Biochim, Biophys. Acta.*, 1126:135-142.

Watson et al., 1987, *Molecular Biology of the Gene*, 46th Ed., Benjamin Cummins.

(56) References Cited

OTHER PUBLICATIONS

Xu et al., 2003, Site-Directed Mutagenesis Using the Megaprimer Method, *Mol. Bio.*, 235:203-207.
Yanisch-Perron et al., 1985, Improved M13 phage cloning vectors and host strains: nucleotide sequences of the M13mp18 and pUC19 vectors, *Gene*, 33:103-119.
Young et al., 1961, Physiological and Genetic Factors Affecting Transformation of *Bacillus subtilis*, *Journal of Bacteriology*, 81:823-829.
Yuan et al., 1995, Modification of the substrate specificity of an acyl-acyl carrier protein thioesterase by protein engineering, *Proc. Natl. Acad. Sci. USA*, 92:10639-10643.

* cited by examiner

FIG. 2

```
  1 CCCGGGAGGA GGATTATAAA ATGACTCTAG AGTGGAAACC GAAACCAAAA
 51 CTGCCTCAAC TGCTGGATGA TCACTTCGTT CTGCACGGTC TGGTGTTTCG
101 TCGTACTTTC GCAATTCGTT CTTATGAAGT GGGTCCAGAT CGTTCTACCT
151 CCATCCTGGC CGTCATGAAC CACATGCAGG AAGCCACCCT GAATCACGCG
201 AAATCTGTTG GTATCCTGGG TGATGGTTTC GGCACTACTC TGGAAATGTC
251 TAAACGTGAC CTGATGTGGG TAGTGCGTCG CACCCACGTA GCAGTAGAGC
301 GCTACCCTAC TTGGGGTGAC ACTGTGGAAG TCGAGTGTTG GATTGGCGCG
351 TCCGGTAACA ATGGTATGCG TCGCGATTTT CTGGTCCGTG ACTGTAAAAC
401 GGGCGAAATC CTGACGCGTT GCACCTCCCT GAGCGTTCTG ATGAACACCC
451 GCACTCGTCG CCTGTCTACC ATCCCGGACG AAGTGCGCGG TGAGATCGGT
501 CCTGCTTTCA TCGATAACGT GGCAGTTAAA GACGACGAAA TCAAGAAACT
551 GCAAAAACTG AACGACTCCA CCGCGGACTA CATCCAGGGC GGTCTGACTC
601 CGCGCTGGAA CGACCTGGAT GTTAATCAGC ATGTGAACAA CCTGAAATAC
651 GTTGCTTGGG TCTTCGAGAC TGTGCCGGAC AGCATTTTCG AAAGCCATCA
701 CATTTCCTCT TTTACTCTGG AGTACCGTCG CGAATGTACT CGCGACTCCG
751 TTCTGCGCAG CCTGACCACC GTAAGCGGCG GTTCTAGCGA GGCAGGTCTG
801 GTCTGCGACC ATCTGCTGCA ACTGGAAGGC GGCTCCGAAG TCCTGCGTGC
851 GCGTACGGAG TGGCGTCCAA AGCTGACGGA TTCTTTCCGC GGCATCTCCG
901 TAATTCCGGC GGAACCTCGT GTTTAAGCTT (SEQ ID NO: 1)
```

FATTY ACID-PRODUCING HOSTS

CROSS REFERENCE TO RELATED APPLICATIONS

This application claims priority under 35 USC §119(e) to U.S. Provisional Patent Application 61/292,918 filed Jan. 7, 2010, the entirety of which is incorporated herein by reference.

FEDERAL FUNDING STATEMENT

This invention was made with government support under DE-FC02-07ER64494 and DE-FG02-03ER15468 awarded by the US Department of Energy. The government has certain rights in the invention.

FIELD OF THE INVENTION

The invention is directed to genetically modified cells or microorganisms capable of overproducing products from the fatty acid biosynthetic pathway (fatty acids or derivatives thereof).

BACKGROUND

The development of new, renewable sources of transportation fuel is necessary to meet continuing demand in the face of dwindling petroleum supplies while also curbing the release of greenhouse gases. While much focus has been placed on developing biomass-derived gasoline alternatives such as ethanol and other short-chain alcohols, higher energy density distillates such as diesel and jet fuel are required for the heavy transportation sector. Furthermore, diesel engines improve fuel efficiency in small passenger vehicles over gasoline engines, and have already been widely adopted in Europe.

Biofuels such as biodiesel are biodegradable, clean-burning combustible fuels made of medium- to long-chain alkanes and esters. Biodiesel can be used in most internal combustion diesel engines in either a pure form, which is referred to as "neat" biodiesel, or as a mix in any concentration with regular petroleum diesel. An advantage of biodiesel is that it can be generated from non-petroleum sources. Current methods of making biodiesel involve transesterification of triacylglycerides (mainly vegetable oil). However, this leads to a mixture of fatty acid esters and the unwanted side product glycerin, thus, providing a product that is heterogeneous and a waste product that causes economic inefficiencies. In addition, the presence of methyl esters and ethyl esters in traditional biodiesel leads to unwanted gelation properties at or around about 0° C. There exists a need for a source of medium- to long-chain hydrocarbons that does not result in a high concentration of unwanted side products such as glycerin, methyl esters, and ethyl esters.

SUMMARY OF THE INVENTION

The invention is directed to hosts for producing a fatty acid product and methods of use thereof.

One version of the invention includes a host that comprises an exogenous nucleic acid encoding a thioesterase, specifically an acyl-acyl carrier protein thioesterase (EC 3.1.2.14), wherein an acyl-CoA synthetase (EC 6.2.1.3) in the host is functionally deleted. The host is preferably a microorganism such as a bacterium (i.e., *E. coli*) or a yeast. The nucleic acid encoding the thioesterase is preferably a codon-optimized thioesterase derived from *Umbellularia californica*. An example of a nucleic acid encoding a codon-optimized thioesterase is SEQ ID NO:1.

In some versions of the invention, the host includes the nucleic acid encoding the thioesterase at an intermediate copy number. The host preferably includes no more than about 250 copies or, more preferably, about 30 copies of the nucleic acid. The host also preferably includes no less than about 2 copies or, more preferably, about 5 copies of the nucleic acid.

In some versions of the invention, the host is operably connected to an origin of replication derived from a plasmid selected from the group consisting of pBR322, pACYC, pBBR1, and pSC101.

The host is preferably recombinantly stable and/or growth-competent at 37° C.

In some versions of the invention, the host further includes an exogenous nucleic acid encoding an acetyl-CoA carboxylase (EC 6.4.1.2). The nucleic acid encoding the acetyl-CoA carboxylase preferably comprises an artificial operon comprising accA, accB, accC, and accD from *E. coli*. The host may include 150 copies or more of the nucleic acid encoding the acetyl-CoA carboxylase.

The invention is also directed to methods of producing a fatty acid product comprising culturing one or more of the hosts described herein. In some versions, the host is cultured at 37° C. The host is preferably recombinantly stable and/or growth-competent at this temperature.

In some versions, the nucleic acid encoding the thioesterase is operably connected to an inducible promoter, and the method further comprises culturing the host in presence of a sub-saturating amount of an effector of the inducible promoter. In such versions, the nucleic acid encoding the thioesterase may be included in the host at a copy number of 50 or more.

In other versions, the nucleic acid encoding the thioesterase is operably connected to a repressible promoter, and the method further comprises culturing the host in presence of a repressor of the repressible promoter. In such versions, the nucleic acid encoding the thioesterase may be included in the host at a copy number of 50 or more.

The fatty acids or hydrocarbons produced from the hosts or methods described herein can be used in any application where fatty acids and hydrocarbons are conventionally used. Specifically, the fatty acids can be used as dietary supplements, and the hydrocarbons can be used as transportation fuels and solvents.

The objects and advantages of the invention will appear more fully from the following detailed description of the preferred embodiment of the invention made in conjunction with the accompanying drawings.

BRIEF DESCRIPTION OF THE DRAWINGS

FIG. 2 depicts a synthesized DNA encoding an exemplary thioesterase of the current invention (codon-optimized acyl-ACP thioesterase from *U. californica* (BTE); SEQ ID NO:1). Shown are restriction sites at the 5' (XmaI) and 3' (HindIII) ends (italicized; nucleotides 1-6 and 925-930, respectively), an artificial ribosome binding site (nucleotides 7-12), a spacer sequence (nucleotides 13-20), an artificial start codon (bolded; nucleotides 21-23), and two bases (nucleotides 24-25) following the start codon (nucleotides 21-23) and before an XbaI site (nucleotides 26-31) to generate an in-frame sequence. The codon corresponding to histidine-204 is underlined (nucleotides 630-632). The stop codon is bolded (nucleotides 924-926).

DETAILED DESCRIPTION OF THE INVENTION

Abbreviations and Terms

Figure 1:
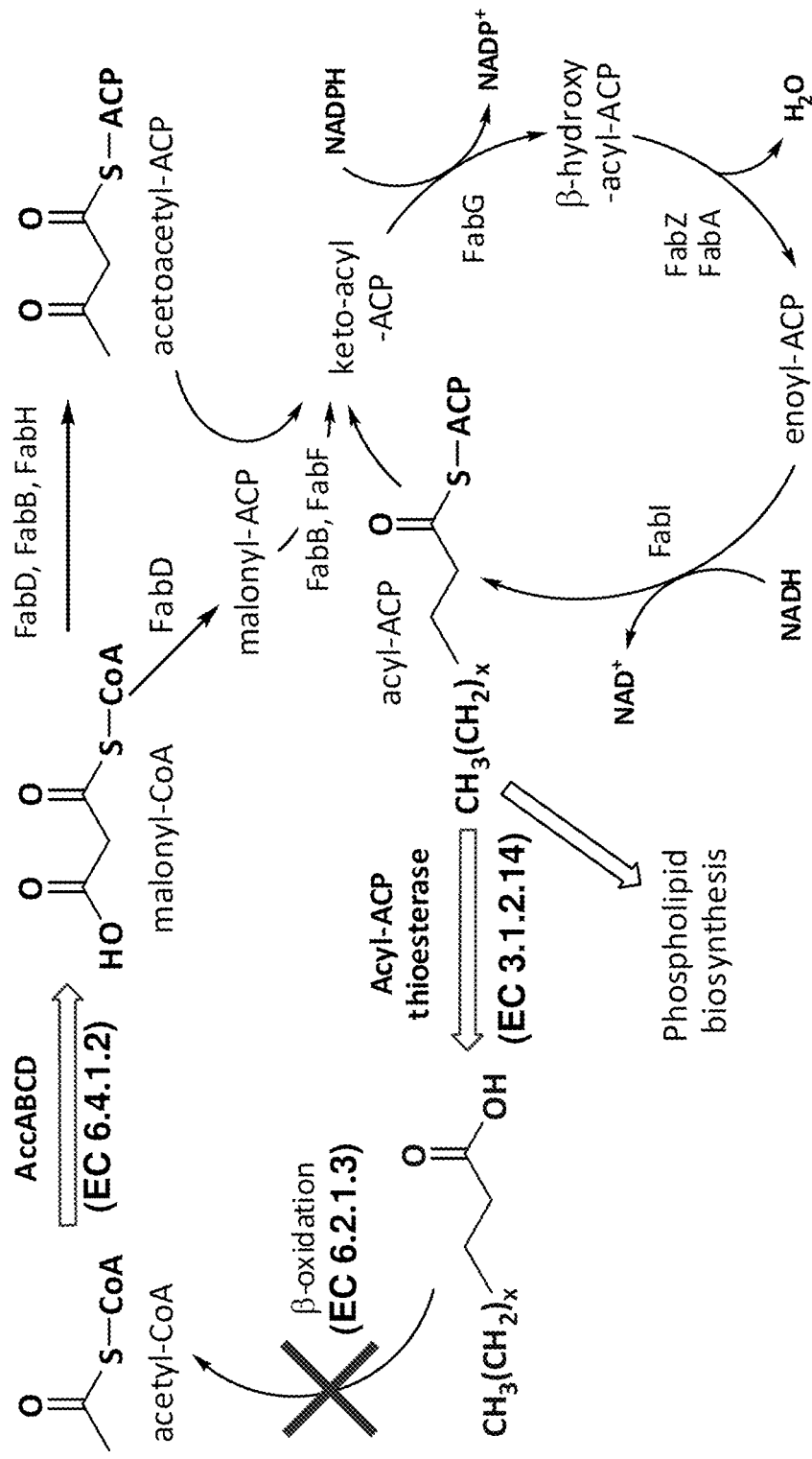
FIG. 1 depicts a schema of the fatty acid biosynthetic pathway with modifications for overproducing fatty acid products. Bolded arrows represent reactions enhanced by overexpression or heterologous expression of indicated enzymes. The X represents a disruption of the indicated pathway by functional deletion.

Accession numbers: The accession numbers throughout this description are derived from the NCBI (National Center for Biotechnology Information) database, maintained by the National Institute of Health, USA, or the KEGG (Kyoto Encyclopedia of Genes and Genomics) database, maintained by the Kyoto Encyclopedia of Genes and Genomics and sponsored in part by the University of Tokyo.

Attenuate: To lessen the impact, activity, or strength of something.

Carbon source: Generally refers to a substrate or compound suitable to be used as a source of carbon for prokaryotic or simple eukaryotic cell growth. Carbon sources can be in various forms, including but not limited to polymers, carbohydrates, acids, alcohols, aldehydes, ketones, amino acids, peptides, etc. These include, for example, various monosaccharides such as glucose, oligosaccharides, polysaccharides, cellulosic material, xylose, and arabinose, disaccharides such as sucrose, saturated or unsaturated fatty acids, succinate, lactate, acetate, ethanol, etc., or mixtures thereof. The carbon source can additionally be a product of photosynthesis, including but not limited to glucose.

Deletion: The removal of one or more nucleotides from a nucleic acid molecule or one or more amino acids from a protein, the regions on either side being joined together.

Derived: When used with reference to a nucleic acid or protein, "derived" means that the nucleic acid or polypeptide is isolated from a described source or is at least 70%, 80%, 90%, 95%, 99%, or more identical to a nucleic acid or polypeptide included in the described source.

Endogenous: As used herein with reference to a nucleic acid molecule and a particular host, "endogenous" refers to a nucleic acid sequence or polypeptide that is in the host and was not introduced into the host using recombinant engineering techniques. For example, an endogenous gene is a gene that was present in a host when the host was originally isolated from nature. A gene is still considered endogenous if the control sequences, such as promoter or enhancer sequences that activate transcription or translation, have been altered through recombinant techniques.

Exogenous: As used herein with reference to a nucleic acid molecule or polypeptide in a particular host, "exogenous" refers to any nucleic acid molecule or polypeptide that does not originate from that particular host as found in nature. Thus, a non-naturally-occurring nucleic acid molecule or protein is considered to be exogenous to a host once introduced into the host. A nucleic acid molecule or protein that is naturally-occurring also can be exogenous to a particular host. For example, an entire coding sequence isolated from cell X is an exogenous nucleic acid with respect to cell Y once that coding sequence is introduced into cell Y, even if X and Y are the same host type. The term "heterologous" is used herein interchangeably with "exogenous."

Expression: The process by which a gene's coded information is converted into the structures and functions of a host, such as a protein, transfer RNA, or ribosomal RNA. Expressed genes include those that are transcribed into mRNA and then translated into protein and those that are transcribed into RNA but not translated into protein (for example, transfer and ribosomal RNAs).

Fatty acid derivative: Includes products other than fatty acids themselves made in part from the fatty acid biosynthetic pathway of a host. Fatty acid derivatives may be generated after extraction of the fatty acids from the host. Alternatively, hosts can be engineered to produce fatty acid derivatives. Exemplary fatty acid derivatives include, for example, short and long chain alcohols, hydrocarbons such as alkanes, and fatty acid esters including waxes.

Fatty acid product: Refers to any fatty acid or derivative thereof produced by a host prior to extraction therefrom. Examples include but are not limited to fatty acids, fatty alcohols, fatty acid esters, waxes, and hydrocarbons. "Fatty acids" include hydroxylated and other forms.

Fermentation broth: Includes any medium which supports host life (i.e., a microorganism that is actively metabolizing carbon). A fermentation medium usually contains a carbon source. The carbon source can be anything that can be used, with or without additional enzymes, by the host for energy.

Functional deletion: Any modification to or treatment of a host that reduces or inhibits production of a gene product, renders the gene product non-functional, or reduces the gene product's activity. One of ordinary skill in the art will appreciate that there are many methods of functionally deleting a gene or gene product. For example, functional deletion can be accomplished by "genetic functional deletion." In general this includes but is not limited to mutations, partial or complete deletions, insertions, or other variations made to a gene sequence or a sequence controlling the transcription of a gene sequence; placing the gene under the control of a less active promoter; and expressing interfering RNA, ribozymes or antisense sequences that target the gene of interest, etc. Functional deletion can also be accomplished by "chemical functional deletion." This includes, for example, chemical inhibition of a gene product with a small-molecular inhibitor.

Host: Any organism, cell, microorganism, etc. undergoing genetic manipulation to increase production of products as described herein. In the preferred version of the invention, the host is a microorganism. Other suitable hosts are described below.

Introduce: When used with reference to genetic material, such as a nucleic acid, and a host, "introduce" refers to the delivery of the genetic material to the host in a manner such that the genetic material is capable of being expressed within the host. Introduction of genetic material includes both transformation and transfection. Transformation encompasses techniques by which a nucleic acid molecule can be introduced into hosts such as prokaryotic cells or non-animal eukaryotic cells. Transfection encompasses techniques by which a nucleic acid molecule can be introduced into hosts such as animal cells. These techniques include but are not limited to introduction of a nucleic acid via conjugation, electroporation, lipofection, infection, and particle gun acceleration.

Isolated: An "isolated" biological component (such as a nucleic acid molecule, polypeptide, or cell) has been substantially separated or purified away from other biological components in which the component naturally occurs, such as other chromosomal and extrachromosomal DNA and RNA and proteins. Nucleic acid molecules and polypeptides that have been "isolated" include nucleic acid molecules and polypeptides purified by standard purification methods. The term also includes nucleic acid molecules and polypeptides prepared by recombinant expression in a host as well as chemically synthesized nucleic acid molecules and polypeptides. In one example, "isolated" refers to a naturally-occurring nucleic acid molecule that is not immediately contiguous with both of the sequences with which it is immediately contiguous (one on the 5' end and one on the 3' end) in the naturally-occurring genome of the organism from which it is derived.

Long-chain fatty acid, fatty acyl-ACP, or fatty acyl-CoA: Includes fatty acids, fatty acyl-ACPs, or fatty acyl-CoAs having a carbon chain longer than 12 carbons.

Medium-chain fatty acid, fatty acyl-ACP, or fatty acyl-CoA: Includes fatty acids, fatty acyl-ACPs, or fatty acyl-CoAs having a carbon chain of 6 to 12 carbons.

Short-Chain fatty acid, fatty acyl-ACP, or fatty acyl-CoA: Includes fatty acids, fatty acyl-ACPs, or fatty acyl-CoAs having a carbon chain fewer than 6 carbons.

Microorganism: Includes prokaryotic and eukaryotic microbial species from the domains Archaea, Bacteria and Eucarya, the latter including yeast and filamentous fungi, protozoa, algae, or higher Protista. The terms "microbial cells" and "microbes" are used interchangeably with the term microorganism.

Nucleic acid: Encompasses both RNA and DNA molecules including, without limitation, cDNA, genomic DNA, and mRNA. Nucleic acids also include synthetic nucleic acid molecules, such as those that are chemically synthesized or recombinantly produced. The nucleic acid can be double-stranded or single-stranded. Where single-stranded, the nucleic acid molecule can be the sense strand, the antisense strand, or both. In addition, the nucleic acid can be circular or linear.

Origin of replication: A particular sequence in a genome or vector (such as a plasmid vector) at which replication is initiated. This can either be DNA replication in living organisms such as prokaryotes and eukaryotes, or RNA replication in RNA viruses, such as double-stranded RNA viruses. The specific structure of the origin of replication varies somewhat from species to species, but all share common characteristics such as high AT content. Various origins of replication are well-defined in the art and are described herein.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. An origin of replication is operably linked to a coding sequence if the origin of replication controls the replication or copy number of the nucleic acid in the host. Operably linked nucleic acids may or may not be contiguous.

Operon: Configurations of separate genes that are transcribed in tandem as a single messenger RNA are denoted as operons. Thus, a set of in-frame genes in close proximity under the transcriptional regulation of a single promoter constitutes an operon. Operons may be synthetically generated using the methods described herein.

Overexpress: When a gene is caused to be transcribed at an elevated rate compared to the endogenous or basal transcription rate for that gene. In some examples, overexpression additionally includes an elevated rate of translation of the gene compared to the endogenous translation rate for that gene. Methods of testing for overexpression are well known in the art, for example transcribed RNA levels can be assessed using rtPCR and protein levels can be assessed using SDS page gel analysis.

Overproduce: In reference to a fatty acid product, "overproduce" refers to an increase in production of a fatty acid product of a host under specific conditions relative to the host in the absence of the same specific conditions. "Specific conditions" refers to genetic modifications as well as non-genetic treatments.

Purified: The term "purified" is understood in its ordinary sense but does not require absolute purity. In one example, a purified fatty acid preparation is one in which the product is more concentrated than the product is in its environment within a cell. In another example, a purified fatty acid is one that is substantially separated from cellular components (nucleic acids, lipids, carbohydrates, and other peptides) that can accompany it in its natural state. In another example, a purified fatty acid is one that is substantially-free from contaminants, such as those that might be present following fermentation. In another example, a fatty acid is purified when at least about 50% by weight of a sample is composed of the fatty acid, for example when at least about 60%, 70%, 80%, 85%, 90%, 92%, 95%, 98%, or 99% or more of a sample is composed of the fatty acid. Examples of methods that can be used to purify fatty acids are described below.

Recombinant: A recombinant nucleic acid molecule or polypeptide is one that has a sequence that is not naturally occurring, has a sequence that is made by an artificial combination of two otherwise separated segments of sequence, or both. This artificial combination can be achieved, for example, by chemical synthesis or by the artificial manipulation of isolated segments of nucleic acid molecules or polypeptides, such as genetic engineering techniques. "Recombinant" is also used to describe nucleic acid molecules that have been artificially manipulated but contain the same regulatory sequences and coding regions that are found in the organism from which the nucleic acid was isolated. A recombinant cell or microorganism is one that contains an exogenous nucleic acid molecule, such as a recombinant nucleic acid molecule.

Saturating amount and variants thereof: As used herein, "saturating amount" refers to a concentration of effector wherein addition of a higher concentration of the effector does not result in an increase in an effect produced by the effector. "Minimal saturating amount" refers to the lowest saturating concentration. "Sub-saturating amount" refers to a concentration lower than the minimal saturating amount, i.e., wherein addition of a higher concentration of effector results in an increase in the effect produced by the effector.

Secondary fatty acid product: A product derived from a fatty acid product after purification from a host or fermentation broth.

Recombinant host: A host into which a nucleic acid molecule has been introduced by molecular biology techniques such as transformation or transfection.

Vector or expression vector: An entity comprising a nucleic acid molecule that is capable of introducing the nucleic acid, or being introduced with the nucleic acid, into a host for expression of the nucleic acid. A vector can include nucleic acid sequences that permit it to replicate in the cell, such as an origin of replication. A vector can also include one or more selectable marker genes and other genetic elements known in the art. Examples of suitable vectors are found below.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below.

The elements and method steps described herein can be used in any combination whether explicitly described or not.

Any version of any method step or element described herein may be used with any other method step or element described herein.

All combinations of method or process steps as described herein can be performed in any order, unless otherwise specified or clearly implied to the contrary by the context in which the referenced combination is made.

As used in this specification and the appended claims, the singular forms "a," "an," and "the" include plural referents unless the content clearly dictates otherwise.

The term "or" is generally employed in its sense including "and/or" unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All publications, patents, and published patent applications are herein expressly incorporated by reference to the same extent as if each individual publication, patent, or published patent application was specifically and individually indicated by reference. In case of conflict between the present disclosure and the incorporated publications, patents, and published patent applications, the present disclosure should control.

The present invention can comprise, consist of, or consist essentially of method steps or elements described herein.

It is understood that the invention is not confined to the particular construction and arrangement of parts herein illustrated and described, but embraces such modified forms thereof as come within the scope of the claims.

Production of Fatty Acids or Derivatives Thereof

To increase production of fatty acids or derivatives thereof (i.e., "fatty acid products") in a host organism, the host organism can be transformed or transfected with exogenous nucleic acids to increase the production of acyl-ACP or acyl-CoA, reduce the catabolism of fatty acid products and intermediates thereof, and/or reduce feedback inhibition at specific points in the biosynthetic pathway. The modifications to the production host described herein can be through genomic alterations, extrachromosomal expression systems, or combinations thereof.

An overview of a preferred modified pathway is provided in FIG. 1. In a native pathway (e.g., in $E.\ coli$), acetyl-CoA is converted to malonyl-CoA by the four subunits of acetyl-CoA carboxylase (AccABCD). Malonyl-CoA is converted to malonyl-ACP by malonyl-CoA:ACP transacylase (FabD), and to the acetoacetyl-ACP, the first β-ketoacyl-ACP in the fatty acid elongation cycle, by multiple pathways catalyzed by FabD, β-ketoacyl-ACP synthase III (FabH), and β-ketoacyl-ACP synthase I (FabB). The ketoacyl-ACP is reduced twice and dehydrated once to yield an acyl-ACP in the elongation cycle by β-ketoacyl-ACP reductase (FabG), enoyl-ACP reductase (FabI), and β-hydroxyacyl-ACP dehydratase (FabZ). The acyl-ACP is then condensed with malonyl-ACP by FabB or β-ketoacyl-ACP synthase II (FabF). Glycerol-3-phosphate acyltransferase (PlsB) and 1-acylglycerol-3-phosphate acyltransferase (PlsC) utilize $C_{16}$ to $C_{18}$ acyl-ACPs as substrates for phospholipid biosynthesis. Acyl-ACP thioesterases hydrolyze acyl-ACPs to yield free fatty acids. Free fatty acids can be degraded, ultimately to acetyl-CoA, by enzymes of β-oxidation. This process is initiated by acyl-CoA synthetase (FadD), which converts free fatty acids to acyl-CoAs. In one version of the invention, this system is modified by expressing an exogenous ACC (AccABCD), expressing an exogenous acyl-ACP thioesterase, and disrupting β-oxidation by functionally deleting such genes (and/or their products) as FadD.

Acetyl-CoA—Malonyl-CoA to Acyl-ACP: Fatty acid synthase (FAS) is a group of peptides that catalyze the initiation and elongation of acyl chains (Marrakchi et al., *Biochemical Society* (2002) 30:1050-1055). The acyl carrier protein (ACP) along with the enzymes in the FAS pathway control the length, degree of saturation, and branching of the fatty acids produced. Enzymes that can be included in FAS include accA, accB, accC, accD, fabD, fabH, fabG, fabA, fabZ, fabI, fabK, fabL, fabM, fabB, and fabF. Depending upon the desired product, one or more of these genes can be attenuated or overexpressed in *E. coli* or other host organisms.

In the preferred version of the invention, genes encoding acetyl-CoA carboxylase (ACC) (EC 6.4.1.2), such as accA, accB, accC, and accD or orthologs thereof, are overexpressed to increase fatty acid production. The ACC genes can be overexpressed by transformation or transfection of exogenous nucleic acids or by other means. The ACC genes or gene products are preferably overexpressed to increase the intracellular concentration thereof by at least 2-fold, such as at least 5-fold or at least 10-fold, relative to native expression levels. Depending on the particular source, ACC exists as a multi-subunit enzyme encoded by separate genes or as a single protein encoded by a single gene. In the latter case, ACC exists in two isoforms, ACC-α and ACC-β. ACC-α is believed to provide malonyl CoA substrate for fatty acid synthesis. ACC-β is believed to provide substrate for mitochondrial fatty acid oxidation. In organisms where such substrate partitioning occurs, it is preferred to use the ACC-α isoform rather than the ACC-β isoform to increase fatty acid production. In organisms where such substrate partitioning does not occur, use of both isoforms is acceptable.

In a preferred version of the invention, the gene encoding ACC is an artificial operon comprising ACC genes derived from *E. coli*: accA, accB, accC, and accD. An exemplary GenBank accession number for genes encoding ACC or subunits thereof for use in the present invention includes but is not limited to AAC73296. Exemplary KEGG accession numbers for genes encoding ACC or subunits thereof for use in the present invention include but are not limited to those listed in Appendix B of U.S. Provisional Patent Application 61/292,918, which is incorporated herein by reference.

In addition to overexpressing ACC, several different modifications can be made to the host strain to obtain an increase fatty acid production. For example, to increase acetyl CoA production, a plasmid with pdh, panK, aceEF (encoding the EIp dehydrogenase component and the E2p dihydrolipoamide acyltransferase component of the pyruvate and 2-oxoglutarate dehydrogenase complexes), fabH/fabD/fabG/acpP/fabF, and/or DNA encoding fatty-acyl-CoA reductases and aldehyde decarbonylases, can be constructed. These genes can all be under the control of a constitutive, or otherwise controllable (inducible or repressible) promoter. Exemplary GenBank accession numbers for these genes are: pdh (BAB34380, AAC73227, AAC73226), panK (also known as coaA, AAC76952), aceEF (AAC73227, AAC73226), fabH (AAC74175), fabD (AAC74176), fabG (AAC74177), acpP (AAC74178), and fabF (AAC74179).

Additionally, fadE, gpsA, ldhA, pflb, adhE, pta, poxB, ackA, ackB, fadA, fadB, plsX, ygiH, fadK, fadJ, and/or fadI can be knocked-out, or their expression levels can be reduced, in the engineered microorganism by transformation with conditionally replicative or non-replicative plasmids containing null or deletion mutations of the corresponding genes, or by substituting promoter or enhancer sequences. Exemplary GenBank accession numbers for these genes are: fadE (AAC73325), gspA (AAC76632), ldhA (AAC74462), pflb (AAC73989), adhE (AAC74323), pta (AAC75357), poxB (AAC73958), ackA (AAC75356), and ackB (BAB81430).

In addition, the plsB D311E mutation (accession number AAC77011) can be used to remove limitations on the pool of acyl-CoA or acyl-acyl carrier protein (acyl-ACP).

The resulting engineered microorganisms can be grown in a desired environment, for example, one with limited glycerol (less than 1% w/v in the culture medium). As such, these microorganisms will have increased acetyl-CoA production levels.

In some embodiments, the intracellular concentration of the biosynthetic pathway intermediate in the host can be increased to further boost the yield of the final product. The intracellular concentration of the intermediate can be increased in a number of ways, including but not limited to increasing the concentration in the culture medium of a substrate for a biosynthetic pathway; increasing the catalytic activity of an enzyme that is active in the biosynthetic pathway; increasing the intracellular amount of a substrate (e.g., a primary substrate) for an enzyme that is active in the biosynthetic pathway; and the like.

Acyl-ACP to Fatty Acid: To engineer a host for the production of a homogeneous population of fatty acid products, one or more thioesterases with a specificity for a particular carbon chain length or chain lengths can be expressed. For example, any of the thioesterases shown in Table 1 can be expressed individually or in combination to increase production of fatty acid products having specific chain lengths.

TABLE 1

Thioesterases.

| Gen Bank Accession Number | Source Organism | Gene | Preferential product produced |
|---|---|---|---|
| AAC73596 | *E. coli* | tesA without leader sequence | $C_8$-$C_{18}$ |
| Q41635; V17097; M94159 | *Umbellularia californica* | fatB | $C_{12:0}$ |
| Q39513 | *Cuphea hookeriana* | fatB2 | $C_{8:0}$-$C_{10:0}$ |
| AAC49269 | *Cuphea hookeriana* | fatB3 | $C_{14:0}$-$C_{16:0}$ |
| Q39473 | *Cinnamonum camphorum* | fatB | $C_{14:0}$ |
| CAA85388 | *Arabidopsis thaliana* | fatB[M141T]* | $C_{16:1}$ |
| NP 189147; NP 193041 | *Arabidopsis thaliana* | fatA | $C_{18:1}$ |
| CAC39106 | *Bradyrhiizobium japonicum* | fatA | $C_{18:1}$ |
| AAC72883 | *Cuphea hookeriana* | fatA | $C_{18:1}$ |

*Mayer et al., BMC Plant Biology 7: 1-11, 2007.

Another thioesterase that can be expressed in a host includes a fatB-type thioesterase specific for C18:1 and C18:0 derived from *Madhuca latifolia*, such as that having the GenBank Accession Number AY835985.

A preferred thioesterase for expression in a host includes a codon-optimized BTE derived from *Umbellularia californica* having the nucleic acid sequence of SEQ ID NO:1 and the polypeptide sequence of SEQ ID NO:2.

Alternatively or additionally, one or more promiscuous thioesterases with a specificity for a wide range of substrates can be used to make a mixture of products having various chain lengths.

Alternatively or additionally, one or more endogenous genes having a specificity for carbon chain lengths other than the desired product's carbon chain length can be attenuated or functionally deleted. For example, $C_{10}$ fatty acid products can be produced by attenuating a thioesterase specific for $C_{18}$ (for example, accession numbers AAC73596 and POADA1), and expressing a thioesterase specific for $C_{10}$ (for example, accession number Q39513). This results in a relatively homogeneous population of fatty acid products that have a carbon chain length of 10. In another example, $C_{14}$ fatty acid products can be produced by attenuating endogenous thioesterases that produce non-$C_{14}$ fatty acids and expressing the thioesterase with accession number Q39473, which uses $C_{14}$-acyl carrier protein (ACP) as a substrate. In yet another example, $C_{12}$ fatty acid products can be produced by expressing thioesterases that use $C_{12}$-ACP as a substrate (for example, accession number Q41635) and attenuating thioesterases that produce non-$C_{12}$ fatty acids.

Additional exemplary KEGG accession numbers for genes of other thioesterases that may be introduced into a cell in the present invention include but are not limited to 55301 (OLAH); 697753 (OLAH); 99035 (Olah); 64669 (Olah); 100027206; 420532 (OLAH); 582714; AT1G08510 (FATB); AT3G25110 (ATFATA); POPTR 412325; POPTR 762721; POPTR 809202; POPTR 831973; 100248960; 100257579 (GSVIVT00016807001); 4340093 (Os06g0143400); 4347505 (Os09g0505300); OSTLU 93278; Dd703 1679; PSEEN2139; Sde 3728; Bamb 6482; Dde 1605; HRM2 18760; Xaut 1005; M446 0169; llmg 1415; M5005 Spy 0766; spyM18 1023; SpyM3 0674; SPs1179; MGAS10270 Spy0883; MGAS10750 Spy0918; MGAS2096 Spy0840; MGAS9429 Spy0881; SpyM50993; M6 Spy0791; M28 Spy0745; Spy49 0820; SP 1408; SPD 1239; spr1265; SPCG 1396; SPG 1349; SPN23F 13730; SPH 1539; SP70585 1447; SPJ 1307; SPP 1427; SPT 0866; SMU.1417c; str1235; stu1235; STER 1215; SSA 1076; SSU98 1449; SGO 1328; SZO 07520; Sez 1208; SEQ 1394; SUB1087; lp 0708 (fat); LJ0432; LBA0386; LSA0345; LSL 1220; Ldb1626; LBUL 1506; LVIS 0609; LSEI 2254; LGAS 0377; Lreu 0335; EF0365; LEUM 0283; CTC00119; CKL 0088; DSY2004; EUBELI 20341; FRAAL2559; FRAAL3859; SACE 2628; SACE 3258; SACE 4275; SACE 4286; PCC8801 3018; Ava 3990; Ava 4730; and Haur 3974.

The modulation of thioesterase expression as described herein can be used to generate a fatty acid with a specific carbon chain length comprising about 35%, 45%, 55%, 65%, 75%, 85%, 95% or more of the total fatty acid population produced. Overproduction of a homogeneous population having similar carbon chain lengths can be verified using methods known in the art, subsequent to cell lysis. See the Examples for preferred methods.

Prevention of fatty acid oxidation: To prevent oxidation of the generated fatty acid products in the cell and thereby allow for a net production of the fatty acid products, an acyl-CoA synthetase in the host can be functionally deleted. Without being limited by mechanism, it is believed that functional deletion of an acyl-CoA synthetase prevents generation of the acyl-CoA oxidation substrates from free fatty acids in the cell. Any method of functionally deleting a gene or gene product described herein or known in the art may be used to functionally delete an acyl-CoA synthetase in the host. For example, cells may be chemically functionally deleted by incubating the cells with inhibitors of acyl-CoA synthetase, such as triacsin A, triacsin C, and enoximone. In the preferred version of the invention, acyl-CoA synthetase is genetically functionally deleted, as described in the Examples. The particular acyl-CoA synthetase gene functionally deleted depends on the particular host harboring the gene.

Non-limiting examples of KEGG accession numbers of genes encoding acyl-CoA synthetases (6.2.1.3) for use in the present invention include 11001 (SLC27A2); 2180 (ACSL1); 2181 (ACSL3); 2182 (ACSL4); 23305 (ACSL6); 51703 (ACSL5); 450739 (ACSL5); 453423 (SLC27A2); 459974 (ACSL3); 461631 (ACSL1);694871; 704908; 706050; 715237 (SLC27A2); 14081 (Acs11); 216739 (Acs16); 26458 (S1c27a2); 433256 (Acs15); 50790 (Acs14); 74205 (Acs13); 113976 (Acs14); 114024 (Acs13); 117243 (Acs16); 25288 (Acs11); 65192 (S1c27a2); 94340 (Acs15); 474670 (ACSL6); 475631 (ACSL1); 477820 (ACSL5); 478298 (SLC27A2); 478927 (ACSL3); 481018 (ACSL4); 100138312 (ACSL3); 506059 (ACSL6); 514159 (ACSL5); 535727 (SLC27A2); 536628 (ACSL4); 537161 (ACSL1); 100157521; 100233169 (ACSL3); 448980 (ACSL4); 494011 (SLC27A2); 100054459; 100056656; 100057925 (ACSL1); 100059190 (ACSL5); 100063361 (ACSL6); 100069953; 100012070; 100013435; 100015666; 100018120; 100025984; 100073630; 100075331; 100080087; 100081479; 100082580; 416324 (ACSL6); 422345 (ACSL4); 422547 (ACSL1); 423896 (RCJMB04_26g6); 424810 (ACSL3); 100217956; 100227254; 100228952; 100229322; 100229545; 100174803; 379352 (MGC53832); 380135 (fac12); 448565 (acs16); 496479; 779783; 393622 (acs14a); 447860; 494096; 555308 (acs11); 559656 (acs13); 566863; 575511; 581020; 590937; 592091; Dmel_CG12512; Dmel_CG3961; Dmel_CG8732;(1(2)44DEa); 409515; C46F4.2 (acs-17); F28F8.2 (acs-2); F37C12.7 (acs-16); F47G6.2; R07C3.4; R09E10.3; R09E10.4; T08B1.6; Y65B4BL.5 (acs-13); Y76A2B.3 (acs-14); NEMVE_v1g162278; NEMVE_v1g195566; NEMVE_v1g89846; NEMVE_v1g92170; AT1G49430 (LACS2); AT1G64400; AT1G77590 (LACS9); AT3G05970 (LACS6); AT4G11030; AT4G14070 (AAE15); AT4G23850; AT5G27600 (LACS7); 4324180 (Os01g0655800); 4324393 (Os01g0681200); 4334764 (Os03g0845500); 4338395 (Os05g0317200); 4340187 (Os06g0158000); 4350728 (Os11g0558300); 4351483 (Os12g0143900); 4351610 (Os12g0168700); OSTLU_24496; OSTLU_26758; CME186C; CML197C; CMT459C; YER015W (FAA2); YIL009W (FAA3); YMR246W (FAA4); YOR317W (FAA1); AGOS_ABL018C; AGOS_ADR052W; KLLA0B11572g; KLLA0B12936g; DEHA0B10340g; DEHA0D11022g; DEHA0D11044g; DEHA0G06611g; PICST_35069 (FAA23); PICST_55002 (FAA24); PICST_65071 (FAA4); PICST_89450 (FAA22); CAGL0H09460g; CAGL0I09878g; CAGL0K07293g; YALI0D17864g; SPBC18H10.02 (lcf1); SPBP4H10.11c; NCU04380; NCU06063; MGG_01551; MGG_04956; MGG_07197; AN0609.2; AN6014.2; AN8280.2; AFUA_1G17190; AFUA_2G09910; AFUA_5G04270; AO090011000642; AO090023000529; AO090038000487; AO090102000633; An09g06740; An16g05150; CNC00660; CNI00710; UM04803.1; UM05450.1; ECU10_0890; ECU10_0910; MONBRDRAFT_38583; DDB_0191105 (fcsA); EHI_010560; EHI_025090; EHI_079300; EHI_127830; EHI_131880; EHI_135740; EHI_147010; EHI_148340; EHI_153060; EHI_153720; EHI_188590; MAL3P8.9; PF07_0129; PF14_0751; PF14_0761; PFB0685c; PFB0695c; PFD0085c; PFE1250w; PFL0035c; PFL1880w; PFL2570w; PY00791; PY01239; TA15995; TA18970; TA20445; TP01_0119; TP01_0520; TP02_0107; cgd3_640; cgd4_3400; cgd5_3200; Chro.30084; Chro.50052; TTHERM_00052710; TTHERM_00083310; TTHERM_00083320; TTHERM_00113020; TTHERM_00187190; TTHERM_00187210; TTHERM_00187230; TTHERM_00187270; TTHERM_00349120; TTHERM_00382380; TTHERM_00678360; TTHERM_00790570; TTHERM_00822110; TTHERM_01066950; TTHERM_01124100; TTHERM_

01250050; Tb09.160.2770; Tb09.160.2780; Tb09.160.2810; Tb09.160.2840; Tb10.70.4200; Tb11.02.2070; 504089.40; 504177.10; 504177.20; 506261.10; 506829.100; 510151.10; 511581.10; LmjF01.0470; LmjF01.0490; LmjF01.0500; LmjF01.0520; LmjF01.0530; LmjF03.0230; LmjF13.0420; TVAG_069460; TVAG_230940; TVAG_320050; TVAG_337850; TVAG_340550; TVAG_405380; TVAG_464410; TVAG_481370; b1805 (fadD); JW1794 (fadD); ECDH10B_1943 (fadD); BWG_1618 (fadD); Z2848 (fadD); ECs2514; ECH74115_2532 (fadD); E2348C_1928 (fadD); c2209 (fadD); UTI89_C1999 (fadD); ECP_1748; APECO1_863 (fadD); EcE24377A_2031 (fadD); EcHS_A1893 (fadD); EcSMS35_1383 (fadD); ECSE_1979; EcolC_1828; EC55989_1978 (fadD); ECED1_2008 (fadD); ECIAI1_1874 (fadD); ECIAI39_1248 (fadD); ECS88_1857 (fadD); ECUMN_2097 (fadD); B21_01763 (fadD); ECBD_1837; ECB_01775 (fadD); EFER_1275 (fadD); STY1948 (fadD); t1059 (fadD); SPA1055 (fadD); SSPA0985; SPAB_01397; SPC_1912 (fadD); SC1811 (fadD); SeHA_C2018; SNSL254_A1958; SeSA_A1961; SeAg_B1314; SeD_A1498; SG1299 (fadD); SEN1219 (fadD); STM1818 (fadD); YP00537; YP02074 (fadD); y2236 (fadD); y3641; YP_1917 (fadD); YP_3645 (fAA1); YPA_1457; YPA_3561; YPN_0406; YPN_1551; YPDSF_1047; YPDSF_3104; YpAngola_A2403 (fadD); YpAngola_A2933; YPTB0674; YPTB2057 (fadD); YpsIP31758_2014 (fadD); YpsIP31758_3402; YPK_2125; YPK_3532; YPTS_0701; YPTS_2118; YE0656; YE2375 (fadD); SF1423 (fadD); S1538 (fadD); SFV_1424 (fadD); SSON_1356 (fadD); SBO_1283 (fadD); SbBS512_E2065 (fadD); SDY_1709 (fadD); ECA2372 (fadD); ECA3830; ETA_15330 (fadD); plu2134 (fadD); plu3671 (fadD); Ent638_2375; ESA_01455; KPN_02322 (fadD); KPK_1971 (fadD); KP1_3447 (fadD); Spro_0747; Spro_2474; Spro_2760; PMI1166 (fadD); PMI2081; HI0002; HI0390.1; (fadD); NTHI0002; NTHI0510 (lcfA); CGSHiEE_01050; CGSHiEE_03310; CGSHiGG_02470; HAPS_1695; HS_0735 (fadD); HSM_1202; PM0707 (fadD_1); PM0925 (fadD_2); MS1358 (caiC); MS2265 (fAA1); APL_0397 (lcfA); APL_1413; APJL_0418 (lcfA); APJL_1445 (fAA1); APP7_0421; APP7_1520; Asuc_1110; NT05HA_0066; XF0287; PD0233 (rpfB); Xfasm12_0252; XfasM23_0222; XCC1858 (rpfB); XC_2331; xccb100_2146; XCV1921 (rpfB); XAC1880 (rpfB); XOO2868 (rpm); XOO_2722; PXO_00067 (rpfB); Smlt2236a (fadD); Smal_1831; VC1985; VC2484; VC0395_A1570 (fadD); VC0395_A2060; VV1_0136; VV1_0649; VV0494; VV1053; VP0351; VP0870; VP1964; VPA1152; VIBHAR_00824; VIBHAR_01379; VS_2220; VF_0533; VF_1708 (fadD); VF_2256; VF_2264; VFMJ11_1834; VFMJ11_2368; VFMJ11_2376; VSAL_I2699; PBPRA0424; PBPRA1075; PBPRA1287; PA3299 (fadD1); PA3300 (fadD2); PA14_21340 (fadD2); PA14_21370 (fadD1); PSPA7_1824 (fadD2); PSPA7_1825 (fadD1); PLES_17671 (fadD1); PP_4549 (fadD); PP_4550 (fadD2); Pput_1339; Pput_1340; PputGB1_4056; PputGB1_4057; PputW619_3844; PputW619_3845; PSPTO_4097 (fadD-1); PSPTO_4098 (fadD-2); Psyr_3834; Psyr_3836; PSPPH_1426 (fadD1); PSPPH_1427(fadD2) PFL_2943 (fadD-2); PFL_3528; PFL_4598 (fadD-2); PFL_4599 (fadD-2); Pfl01_4353; Pfl01_4354; PSEEN2544; PSEEN3973 (fadD); PSEEN3975 (fadD2); Pmen_1495; Pmen_1496; Pmen_2970; PST_2960 (fadD1); PST_2961; CJA_1075 (fadD); Psyc_1866; Psyc_1867 (fadD1); PsycPRwf_2192; ACIAD0235; ACIAD1572; A1S_1815; ABSDF0218 (fadD); ABAYE3678 (fadD); SO_0075; SO_2581 (fadD-1); SO_3664 (fadD-2); Sden_0072; Sden_1625; Sden_2934; Sfri_1733; Sfri_3973; Sama_1934; Sama_2897; Sama_3571; Sbal_0956; Sbal_1864; Sbal_4274; Shew185_0075; Shew185_1025; Shew185_1891; Sbal195_0080; Sbal195_1058; Sbal195_1898; Sba1223_0077; Sba1223_2428; Shew_2188; Shew_2610; Shew_3084; Shew_3776; Sputcn32_0061; Sputcn32_0970; Sputcn32_1761; Ssed_1667; Ssed_2523; Ssed_3136; Ssed_3695; Ssed_4459; Spea_2448; Shewmr4_0078; Shewmr4_2177; Shewmr7_0076; Shewmr7_2254; Shewana3_0080; Shewana3_2386; Shewana3_3231; Sputw3181_2264; Sputw3181_4017; Shal_0063; Shal_1832; Swoo_2110; swp_0114; swp_2289; IL1827 (fadD); CPS_1189 (fadD1); CPS_3416; CPS_3427 (fadD2); PSHAa2134; PSHAb0502 (fadD); Patl_0322; Patl_1368; Patl_2804; Sde_1886; Maqu_1593; MADE_01137; Ping_1014; Ping_2606; lpg1127; lpg1554 (fadD-1); lpg2230; lpl1133; lpl1472 (fadD); lpl2155; lpp1128; lpp1511 (fadD); lpp2182; LPC_0976 (fadD-1); LPC_1697; MCA1006; MCA1569; FTT1254 (fadD1); FTT1528 (fadD2); FTF1254 (fadD1); FTF1528 (fadD2); FTW_0403; FTW_0690; FTL_0586; FTL_0690; FTH_0586 (fadD1); FTH_0692 (caiC); FTA_0620; FTA_0728; FTM_0370 (fadD); FTM_1112; FTN_1273; FTN_1436 (fadD); Fphi_1239; Fphi_1411; Noc_0825; Noc_2380; Mlg_1601; Mlg_2127; Hhal_0052; Hhal_2209; HCH_02646; HCH_04499; HCH_04890; Csal_1468; ABO_0184 (fadB) AHA_0722; AHA_1893; AHA_2204; ASA_0719 (faal); ASA_2095 (fadD); ASA_2411; DNO_1002; Lferr_0397; AFE_0220; NMB1276 (fadD-1); NMB1555 (fadD-2); NMA1482; NMA1743; NMC1207; NMC1472 (fadD); NMCC_1187 (fadD1); NMCC_1457 (fadD2); NG00530; NGO1213; NGK_0299; NGK_1402; CV_0093 (fadD1); CV_1459 (fadD2); CV_4051; LHK_00715; RSc0064; RSc2857 (fadD1); Rpic_0413; Rpic_3104; Rpic_3685; Reut_A0260; Reut_A2994; Reut_A3057; Reut_B3549; Reut_B3565; Reut_B3605; Reut_B4042; Reut_B4155; Reut_B4758; Reut_C6056; Reut_C6065; Reut_C6185; Reut_D6480; H16_A0285; H16_A1295; H16_A2150; H16_A2748; H16_A2947; H16_A3288 (fadD3); H16_A3351; H16_B0753; H16_B1239; H16_B1736; Rmet_0214; Rmet_2525; Rmet_3148; Rmet_3215; Rmet_4068; Rmet_4454; Rmet_4502; Rmet_4746; Rmet_5140; Rmet_5528; Rmet_5827; RALTA_A025; BMA1134; BMAl276 (fadD); BMASAVP1_A1764 (fadD); BMA10229_A0131 (fadD); BMA10247_1035 (fadD); BPSL1734; BPSL1883; BPSL3037 (fadD); BURPS1710b_1957; BURPS 1710b_3556; BURPS 1710b_A1154; BURPS 1106A_1803 (fadD); BURPS1106A_3563; BURPS668_1782 (fadD); BURPS668_3537; BURPS668_A2935; BTHI1106; BTH_I2529; Bcep1808_0523; Bcep1808_1500; Bcep1808_5414; Bcep18194_A4674; Bcep18194_C6801; Bcep18194_C6813; Bcen_1054; Bcen2424_1534; Bcen2424_3256; Bcen2424_6272; Bcenmc03_1510; BCAL1541; Bamb_0451; Bamb_1416; BamMC406_0476; BamMC406_1456; Bmul_1720; Bmul_2848; BMULJ_00390 (fadD); BMULJ_01520 (fadD); Bxe_A0474; Bxe_A2746; Bxe_A2778; Bxe_B0702; Bxe_B2539; Bxe_CO318; Bxe_C0707; Bxe_C0867; Bphy_1704; Bphy_2685; Bphyt_1672; Bphyt_3482; BP0532; BP1099; BP2811 (fadD); BPP0229; BPP0915; BPP2042; BPP2338 (fadD); BPP3729 (fadD2); BB0233; BB1125; BB1789 (fadD); BB2290; BB4175 (fadD2); Bpet3416 (fadD); Bpet4743; BAV0187; Rfer_2283; Rfer_3503; Rfer_3542; Rfer_3752; Rfer_3775; Rfer_3898; Rfer_4067; Bpro_0604; Bpro_3837; Bpro_4543; Pnap_0267; Pnap_1168; Pnap_3607; Pnap_3797; Aave_0787; Aave_

4574; Ajs_0470; Ajs_0653; Ajs_2038; Ajs_2318; Ajs_3950; Veis_1683; Veis_2551; Veis_2725; Veis_3437; Veis_4099; Daci_0027; Daci_0946; Daci_1072; Daci_1159; Daci_3751; Dtpsy_0461; Mpe_A0353; Mpe_A2687; Mpe_A3572; HEAR0221 (fadD); mma_0275 (fadD); Lcho_0424; Lcho_3434; NE1549; NE2235; Neut_0702; Nmul_A0095; Nmul_A1417; ebA4749; azo1033 (fadD1); azo3447 (acS2); Daro_0249; Daro_1553; Daro_2355; Tmz1t_0406; Tbd_2597; CAP2UW1_1611; WS0237; CFF8240_1668; CCV52592_1489; CCC13826_1773 (cysE); NIS_0535; SUN_0875; SUN_1131; SUN_2246; GSU1677; Gmet_1469; Gura_1590; Gbem_2125; GM21_2093; Pcar_1619; Ppro_3483; DVU1453 (fadD); DVU3119; Dvul_0263; Dvul_1626; Dde_0193; Dde_1725; Dbac_2282; Bd1803 (fadD); Bd3149; DP0067; DP0555; DP1333; Dole_3006; Dalk_0066; Dalk_3803; Adeh_1165; Adeh_2345; Adeh_2359; Adeh_2886; A2cp1_1619; Anae109_1212; Anae109_1529; AnaeK_1524; MXAN_1528; MXAN_2959; sce8696; SYN_02640; SYN_02643; SYN_03128; Sfum_0108; SAR11_0422 (faal); m115415; Meso_0069; SMc02162 (fadD); Smed_0110; Atu0405 (fadD); AGR_C_713; RHE_PF00013 (ypf00005); Oant_0373; b110994; bll1319 (fadD); bll7820; bll7928; blr1288; blr2951; blr5963; blr7807; BRADO0982; BRADO2579; BRADO5264; BRADO6584 (fadD); BRADO6752; BRADO6869; BBta_0674; BBta_0681; BBta_0779; BBta_0952 (fadD); BBta_2927; BBta_5715; BBta_7073; RPA0464; RPA1234; RPA1242 (fadD1); RPA1766; RPA2142; RPA3299; RPA3465; RPA3716 (pimA); RPA4042; RPA4267; RPA4823; RPB_1344; RPB_1560; RPB_1747; RPB_3597; RPB_4080; RPB_4700; RPC_0861; RPC_1049; RPC_2227; RPC_3202; RPC_4074; RPC_4176; RPD_1323; RPD_1569; RPD_3552; RPD_4410; RPE_1707; RPE_1783; RPE_2253; RPE_2373; RPE_3779; RPE_4227; RPE_4911; Rpal_4572; Rpal_4746; Nwi_2684; Nham_3734; OCAR_7378; Xaut_5039; Mext_0124; Mext_3653; M446_2308; Mchl_3946; CC_0944; CC_0966; CC_1321; SPO1847; SPO3003; SPO3296; TM1040_0113; TM1040_2789; TM1040_3271; RSP_2279; Rsph17029_0954; Rsph17025_2217; Jann_4012; RD1_0546 (fadD); RD1_0702; RD1_2849; Pden_0048; Dshi_0373; Dshi_1000; Saro_0191; Sala_0169; Sala_0682; Swit_0282; Swit_2949; ELI_12825; ELI_13210; Acry_0254; Acry_0662; Acry_1256; Rru_A1312; Rru_A2191; Rru_A3509; amb3589; Mmc1_3555; BSU10270 (yhfL); BSU28560 (lcfA); BH2006; BH3103; BH3104; BA0876; BA1091; BA3688; BA4763 (fadD); GBAA0876; GBAA1091; GBAA3688; GBAA4763 (fadD); BA_1642; BA_5193; BAS0832; BAS1019; BAS3419; BAS4422; BAMEG_4797; BAA_4778 (fadD); BC1088; BC3628; BC4526; BCE_0965; BCE_1193; BCE_3436; BCE_3647; BCE_4653 (fadD); BCZK1006 (fadD); BCZK4273 (lcfA); BCAH187_A1250; BCAH187_A4654 (fadD); BCB4264_A1123; BCB4264_A4634 (fadD); BCAH820_4638 (fadD); BCG9842_B0601 (fadD); BCQ_4334 (lcfA); BCA_4632 (fadD); Bcer98_0840; Bcer98_3226; BT9727_1003 (fadD); BT9727_4261 (lcfA); BALH_0970 (fadD); BALH_3074; BALH_4110 (lcfA); BcerKBAB4_1008; BcerKBAB4_4354; BL00331 (lcfA); BL01080 (yhfL); BL01325 (ynglA); BLi01103 (yhfL); BLiO3003 (lcfA); ABC2673 (lcfA); ABC3618; RBAM_010470 (yhfL); BPUM_0969 (lcfA1); BPUM_2513 (lcfA2); OB1176; OB2122; GK0668; GK1030; GK1491; GK2136; GK2690; GK2782; GTNG_0575; GTNG_0892; GTNG_2617; Aflv_0564 (lcfA); Aflv_2253; SA0226; SAV0234; MW0210; SAR0226 (fadE); SAS0210; SACOL0214; SAB0173c; SAB0525; SAOUHSC_00198; SaurJH9_0218; SaurJH1_0224; NWMN_0170 (fadE); SSP2426; Bsph_0428; Bsph_4064; Exig_0720; Exig_2168; EAT1b_2611; BBR47_16670 (lcfA); Pjdr2_0492; llmg_1965; M5005_Spy_0433; MGAS10270_Spy0434; MGAS10750_Spy0453; MGAS2096_Spy0452; MGAS9429_Spy0432; SpyM51431; M6_Spy0467; M28_Spy0421; Cthe_1232; STH3016 STH619 STH704; DSY0943; DSY2317; DSY2479; DSY4298; Dred_2963; PTH_1376 (caiC); HM1_0075 (lcfA); HM1_0197 (fadD); TTE1960 (caiC); Teth514_1062; Teth39_0579; CHY_0437 (fadD1); CHY_0845 (fadD2); CHY_1613; CHY_1731 (fadD3); CHY_1735 (fadD4); CHY_2411 (fadD5); Moth_0503; Rv2187 (fadD15); MT0224; MT2242; MRA_2202 (fadD15); TBFG_12215; Mb0220 (fadD4); Mb2209; Mb2210 (fadD15); BCG_2202; BCG_2203 (fadD15); ML0887; MLBr_00887; MAP1925 (fadD15); MAP3601 (fadD5); MAP3649 (fadD4); MAV_2307; MAV_5077; MSMEG_4254; MUL_3431; MUL_3542 (fadD15); Mvan_1594; Mflv_2962; MAB_1978c; Mmcs_3282; Mkms_3344; Mjls_3293; Mjls_3607; MMAR_1606; MMAR_3231 (fadD15); NCg10279 (cg10284); NCg10388 (cg10400); NCg12216 (cg12296); cg0480 (fadD5); cg2521 (fadD15); cg3179 (fadD2); cgR_0472; cgR_2168; CE0421; CE2195; DIP0386; DIP0387; DIP1725; jk0597 (fadD3); jk1915 (fadD6); jk2042 (fadD7); nfa30980; nfa47040; nfa5250; RHA1_ro01121; RHA1_ro01496; RHA1_ro01533; RHA1_ro01899; RHA1_ro03009; RHA1_ro03747; RHA1_ro03779; RHA1_ro04492; RHA1_ro06034; RHA1_ro06989; RHA1_ro08945; RHA1_ro10229; RHA1_ro10297; ROP_35670; SCO2131 (SC6G10.04); SCO2561 (SCC77.28c); SCO2720 (SCC46.05c); SC06552 (SC4B5.02c); SC06968 (SC6F7.21); SAV_1259 (fadD6); SAV_1603 (fadD7); SAV_1848 (fadD8); SAV_377 (fadD1); SAV_4818 (fadD10); SAV_5562 (fadD12); SAV_605 (fadD2); SAV_6069 (fadD14); SAV_6612 (fadD15); SGR_4985; SGR_5372; Lxx15440 (fadD); CMM_1414; CMM_1418; CMM_1877; CMM_2418 (fadD); CMS_1354; Arth_1547; Arth_3583; AAur_1687; RSa133209_0755; RSa133209_2519; KRH_03520 (fadD); KRH_15020; KRH_15500 (fadD); PPA1632; PPA1724; PPA2234; Noca_2616; Noca_2618; Noca_3113; Noca_4335; Tfu_1031; Tfu_1998; Tfu_2158; Francci3_2245; Francci3_3097; Franean1_1820; FRAAL2616; FRAAL3190; FRAAL5098; Krad_3241; Krad_3506; SACE_1193 (fadD); SACE_1694; SACE_3153; SACE_3409; SACE_3444; SACE_3478; SACE_4038 (fadD); SACE_5343; SACE_5393; Amir_1383; Strop_2082; Strop_2641; Strop_3277; Sare_3509; BL0266 (fadD1); BL0858 (fadD2); BL1501 (fadD3); BL1748 (fadD4); BAD_0724 (fadD2); BAD_0774 (fadD4); BAD_0779 (fadD3); BAD_1409 (fadD1); Rxyl_2060; BG0139; BG0606; BAPKO_0139; BAPKO_0624; TDE1742; TDE2186; LA0106; LA2177; LA2309; LB093 (fadD); LIC10094; LIC11630 (fadD); LIC11747 (ydiD); LIC20074; LBJ_0086; LBJ_1312; LBL_0050; LBL_1537; Acid345_2081; Acid345_2858; ACP_0820; Acid_1327; Acid_5700; BT_0684; BT_2154; BT_3550; BF0373; BF3857; BF0320; BF3628; BVU_3870; PG1145; PG1829; BDI_0527; SRU_1209 (fadD); SRU_2380; CHU_3595 (fadD); Cpin_1114; GFO_1049 (fadD); Fjoh_4728; FP1720 (fadD); Coch_1374; Coch_1523; FN0867; FN1122; RB8524 (lcfA); Emin_1237; slr1609; SYNW0669 (fadD); syc0624_c (fadD); Synpcc7942_0918; Syncc9605_2011; Syncc9902_0660; sync_0608 (fadD-1); sync_1515 (fadD- 2); SynRCC307_1796 (fadD); SynWH7803_0580 (fadD); SYNPCC7002_A0675 (fadD); CYA_0133; CYB_2181; tll1301; MAE_58850; cce_1133 (fadD); gll1950; g1r0435; g1r1146; a1r3602; Ava_3173; Pro0399 (fAA1); PMM0402 (fadD); PMT0215 (fadD); PMN2A_1737; PMT9312_0398; A9601_04531 (fadD); P9515_04641 (fadD); P9303_21391 (fadD); P9301_04221 (fadD); P9215_04791 (fadD); NATL1_04541 (fadD); AM1_5562; CT0046 (fadD); CT1156; Cpar_1101; Cag_1135; Cpha266_1519; Cpha266_2588; Cphamn1_1299; Clim_1391; Cvib_0930; Plut_0972; Plut_2064; Ppha_1487; Paes_1021; Ctha_2084; Ctha_2252; DET0946; DET1033; cbdb_A1006; cbdb_A901; DehaBAV1_0830; DehaBAV1_0916; RoseRS_0623; RoseRS_1007; RoseRS_2084; RoseRS_2094; Rcas_0545; Rcas_1775; Rcas_3335; Caur_1072; Caur_1085; Cagg_2424; Chy400_1187; Haur_3729; Haur_4238; DR_1692; DR_A0309; Dgeo_1070; TTC0079; TTC0217; TTC1065; TTC1099; TTHA0448; TTHA0586; TTHA1430; TTHA1463; aq_999 (fadD); Mhun_2450; AF1029 (fadD-5); AF1772 (fadD-7); VNG1339C; VNG2071G (lf12); OE2912F (acs3); OE3891R (acs5); rrnAC1074 (fadD3); NP2626A (alkK_1); NP3386A (alkK_4); NP4174A (lfl); NP4256A (alkK_2); APE_1307; APE_1310; APE_2284.1 (fadD); SSO0369 (fadD-1); SSO3064 (fadD-3); ST1112; ST1388; Saci_1966 (fadD); Saci_2207; Msed_1015; Msed_1615; PAE1379; PAE2466; Pis1_1435; Pcal_0839; and Pars_0455.

Genetic Engineering of Host to Increase Fatty Acid Product Production

Exogenous nucleic acids encoding enzymes involved in a biosynthetic pathway for the production of fatty acid products can be introduced stably or transiently into a host using techniques well known in the art, including electroporation, calcium phosphate precipitation, DEAE-dextran mediated transfection, liposome-mediated transfection, conjugation, transduction, and the like. For stable transformation, a nucleic acid can further include a selectable marker. Suitable selectable markers include antibiotic resistance genes that confer, for example, resistance to neomycin, tetracycline, chloramphenicol, or kanamycin, genes that complement auxotrophic deficiencies, and the like. (See below for more detail.)

Various embodiments of the invention use an expression vector that includes a heterologous nucleic acid encoding a protein involved in a metabolic or biosynthetic pathway. Suitable expression vectors include, but are not limited to viral vectors, such as baculovirus vectors or those based on vaccinia virus, polio virus, adenovirus, adeno-associated virus, SV40, herpes simplex virus, and the like; phage vectors, such as bacteriophage vectors; plasmids; phagemids; cosmids; fosmids; bacterial artificial chromosomes; P1-based artificial chromosomes; yeast plasmids; yeast artificial chromosomes; and any other vectors specific for hosts of interest (such as E. coli, Pseudomonas pisum, or Saccharomyces cerevisiae).

Useful vectors can include one or more selectable marker genes to provide a phenotypic trait for selection of transformed hosts. The selectable marker gene encodes a protein necessary for the survival or growth of transformed hosts grown in a selective culture medium. Hosts not transformed with the vector containing the selectable marker gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. In alternative embodiments, the selectable marker gene is one that encodes dihydrofolate reductase or confers neomycin resistance (for use in eukaryotic cell culture), or one that confers tetracycline or ampicillin resistance (for use in a prokaryotic host, such as E. coli).

The biosynthetic pathway gene product-encoding nucleic acid in the expression vector is operably linked to an appropriate expression control sequence (promoters, enhancers, and the like) to direct synthesis of the encoded gene product. Such promoters can be derived from microbial or viral sources, including CMV and SV40. Depending on the host/vector system utilized, any of a number of suitable transcription and translation control elements, including constitutive and inducible promoters, transcription enhancer elements, transcription terminators, etc. can be used in the expression vector (see e.g., Bitter et al. (1987) *Methods in Enzymology*, 153:516-544).

Suitable promoters for use in prokaryotic hosts include but are not limited to: promoters capable of recognizing the T4, T3, Sp6, and T7 polymerases; the $P_R$ and $P_L$ promoters of bacteriophage lambda; the trp, recA, heat shock, and lacZ promoters of E. coli; the alpha-amylase and the sigma-specific promoters of B. subtilis; the promoters of the bacteriophages of Bacillus; Streptomyces promoters; the int promoter of bacteriophage lambda; the bla promoter of the beta-lactamase gene of pBR322; and the CAT promoter of the chloramphenicol acetyl transferase gene. Prokaryotic promoters are reviewed by Glick, *J. Ind. Microbiol.* 1:277 (1987); Watson et al, Molecular Biology of the Gene, 4th Ed., Benjamin Cummins (1987); and Sambrook et al., In: *Molecular Cloning: A Laboratory Manual*, 3rd ed., Cold Spring Harbor Laboratory Press (2001).

Non-limiting examples of suitable promoters for use within a eukaryotic host are typically viral in origin and include the promoter of the mouse metallothionein I gene (Hamer et al. (1982) *J. Mol. Appl. Gen.* 1:273); the TK promoter of Herpes virus (McKnight (1982) *Cell* 31:355); the SV40 early promoter (Benoist et al. (1981) *Nature* (London) 290:304); the Rous sarcoma virus promoter; the cytomegalovirus promoter (Foecking et al. (1980) *Gene* 45:101); the yeast gal4 gene promoter (Johnston et al. (1982) *PNAS* (USA) 79:6971; Silver et al. (1984) *PNAS* (USA) 81:5951); and the IgG promoter (Orlandi et al. (1989) *PNAS* (USA) 86:3833).

The host can be genetically modified with a heterologous nucleic acid encoding a biosynthetic pathway gene product that is operably linked to an inducible promoter. Inducible promoters are those wherein addition of an effector induces expression. Suitable effectors include proteins, metabolites, chemicals, or culture conditions capable of inducing expression. Suitable inducible promoters include but are not limited to the lac promoter (regulated by IPTG or analogs thereof), the lacUV5 promoter (regulated by IPTG or analogs thereof), the tac promoter (regulated by IPTG or analogs thereof), the trc promoter (regulated by IPTG or analogs thereof), the araBAD promoter (regulated by L-arabinose), the phoA promoter (regulated by phosphate starvation), the recA promoter (regulated by nalidixic acid), the proU promoter (regulated by osmolarity changes), the cst-1 promoter (regulated by glucose starvation), the tetA promoter (regulated by tetracycline), the cadA promoter (regulated by pH), the nar promoter (regulated by anaerobic conditions), the $p_L$ promoter (regulated by thermal shift), the cspA promoter (regulated by thermal shift), the T7 promoter (regulated by thermal shift), the T7-lac promoter (regulated by IPTG), the T3-lac promoter (regulated by IPTG), the T5-lac promoter (regulated by IPTG), the T4 gene 32 promoter (regulated by T4 infection), the nprM-lac promoter (regulated by IPTG), the VHb promoter (regulated by oxygen), the metallothionein promoter (regulated by heavy metals), the MMTV promoter promoter (regulated by steroids such as dexamethasone) and variants thereof.

Alternatively, the host can be genetically modified with a heterologous nucleic acid encoding a biosynthetic pathway gene product that is operably linked to a repressible promoter. Repressible promoters are those wherein addition of an effector represses expression. Examples of repressible promoters include but are not limited to the trp promoter (regulated by tryptophan); tetracycline-repressible promoters, such as those employed in the "TET-OFF"-brand system (Clontech, Mountain View, Calif.); and variants thereof.

In some versions, the host is genetically modified with a heterologous nucleic acid encoding a biosynthetic pathway gene product that is operably linked to a constitutive promoter. Suitable constitutive promoters are known in the art and include constitutive adenovirus major late promoter, a constitutive MPSV promoter, and a constitutive CMV promoter.

The relative strength of the promoters described herein are well-known in the art.

In some versions, the host is genetically modified with an exogenous nucleic acid encoding a single protein involved in a biosynthesis pathway. In other embodiments, a modified host is one that is genetically modified with exogenous nucleic acids encoding two or more proteins involved in a biosynthesis pathway.

Where the host is genetically modified to express two or more proteins involved in a biosynthetic pathway, those nucleic acids can each be contained in a single or in separate expression vectors. When the nucleic acids are contained in a single expression vector, the nucleotide sequences may be operably linked to a common control element (e.g., a promoter), that is, the common control element controls expression of all of the biosynthetic pathway protein-encoding nucleic acids in the single expression vector.

When the host is genetically modified with heterologous nucleic acids encoding two or more proteins involved in a biosynthesis pathway, one of the nucleic acids can be operably linked to an inducible promoter, and one or more of the nucleic acids can be operably linked to a constitutive promoter. Alternatively, all can be operably linked to inducible promoters or all can be operably linked to constitutive promoters.

Nucleic acids encoding enzymes desired to be expressed in a host may be codon-optimized for that particular type of host. Codon optimization can be performed for any nucleic acid by "OPTIMUMGENE"-brand gene design system by GenScript (Piscataway, N.J.). An example of a codon-optimized nucleic acid expressing a thioesterase is SEQ ID NO:1. The polypeptide product expressed therefrom is SEQ ID NO:2.

Hosts that may be used as part of the present invention include, without limitation, bacteria, fungi (including yeasts), plant, insect, mammal, or other appropriate animal cells or cell lines. The host is preferably a bacterium or a yeast.

Examples of suitable bacterial hosts include gram-positive bacteria such as strains of *Bacillus*, (e.g., *B. brevis* or *B. subtilis*), *Pseudomonas*, or *Streptomyces*, or gram-negative bacteria, such as strains of *E. coli*. Particularly desirable hosts for expression in this regard include bacteria that do not produce lipopolysaccharide and are, therefore, endotoxin free. The introduction of a vector into a bacterial host may, for instance, be performed by protoplast transformation (Chang and Cohen (1979) *Molecular General Genetics*, 168:111-115), using competent cells (Young and Spizizen (1961) *Journal of Bacteriology*, 81:823-829; Dubnau and Davidoff-Abelson (1971) *Journal of Molecular Biology*, 56: 209-221), electroporation (Shigekawa and Dower (1988) *Biotechniques*, 6:742-751), or conjugation (Koehler and Thorne (1987) *Journal of Bacteriology*, 169:5771-5278). Commercially available vectors for expressing heterologous proteins in bacterial hosts include but are not limited to pZERO, pTrc99A, pUC19, pUC18, pKK223-3, pEX1, pCAL, pET, pSPUTK, pTrxFus, pFastBac, pThioHis, pTrcHis, pTrcHis2, and pLEx, in addition to those described in the examples. For example, the phage in lambda GEM™-11 may be utilized in making recombinant phage vectors which can be used to transform hosts, such as *E. coli* LE392.

Examples of suitable yeast hosts include strains of *Saccharomyces*, such as *S. cerevisiae*; *Schizosaccharomyces*; *Kluyveromyces*; *Pichia*, such as *P. pastoris* or *P. methlanolica*; *Hansenula*, such as *H. Polymorpha*; *Yarrowia*; or *Candida*. Methods for transforming yeast cells with heterologous DNA and producing heterologous polypeptides therefrom are disclosed by Clontech Laboratories, Inc., Palo Alto, Calif., USA (in the product protocol for the "YEASTMAKER"-brand yeast tranformation system kit); Reeves et al. (1992) *FEMS Microbiology Letters* 99:193-198; Manivasakam and Schiestl (1993) *Nucleic Acids Research* 21 (18):4414-5; and Ganeva et al. (1994) *FEMS Microbiology Letters* 121:159-64. Expression and transformation vectors for transformation into many yeast strains are available. For example, expression vectors have been developed for the following yeasts: *Candida albicans* (Kurtz, et al. (1986) *Mol. Cell. Biol.* 6:142); *Candida maltosa* (Kunze et al. (1985) *J. Basic Microbiol.* 25:141); *Hansenula polymorpha* (Gleeson et al. (1986) *J. Gen. Microbiol.* 132:3459) and Roggenkamp et al. (1986) *Mol. Gen. Genet.* 202:302); *Kluyveromyces fragilis* (Das et al. (1984) *J. Bacteriol.* 158:1165); *Kluyveromyces lactis* (De Louvencourt et al. (1983) *J. Bacteriol.* 154:737) and Van den Berg et al. (1990) Bio/Technology 8:135); *Pichia quillerimondii* (Kunze et al. (1985) *J. Basic Microbiol.* 25:141); *Pichia pastoris* (Cregg et al. (1985) *Mol. Cell. Biol.* 5:3376; U.S. Pat. Nos. 4,837,148; and 4,929,555); *Saccharomyces cerevisiae* (Hinnen et al. (1978) *Proc. Natl. Acad. Sci.* USA 75:1929 and Ito et al. (1983) *J. Bacteriol.* 153:163); *Schizosaccharomyces pombe* (Beach et al. (1981) *Nature* 300:706); and *Yarrowia lipolytica* (Davidow et al. (1985) *Curr. Genet.* 10:380-471 and Gaillardin et al. (1985) *Curr. Genet.* 10:49).

Examples of suitable filamentous fungal hosts include strains of *Aspergillus*, e.g., *A. oryzae*, *A. niger*, or *A. nidulans*; *Fusarium* or *Trichoderma*. Fungal cells may be transformed by a process involving protoplast formation, transformation of the protoplasts, and regeneration of the cell wall in a manner known per se. Suitable procedures for transformation of *Aspergillus* hosts are described in EP 238 023 and U.S. Pat. No. 5,679,543. Suitable methods for transforming *Fusarium* species are described by Malardier et al., *Gene*, 1989, 78:147-56 and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al. (1983) *Journal of Bacteriology*, 153: 163; and Hinnen et al. (1978) *PNAS* USA, 75:1920.

Examples of suitable insect hosts include a *Lepidoptora* cell line, such as *Spodoptera frugiperda* (Sf9 or Sf21) or *Trichoplusioa ni* cells ("HIGH FIVE"-brand insect cells, Invitrogen, Carlsbad, Calif.) (U.S. Pat. No. 5,077,214). Transformation of insect cells and production of heterologous polypeptides therein may be performed as described by Invitrogen.

Examples of suitable mammalian hosts include Chinese hamster ovary (CHO) cell lines, e.g., CHO-K1 (ATCC CCL-61); green monkey cell lines, e.g., COS-1 (ATCC CRL-1650) and COS-7 (ATCC CRL-1651); mouse cells, e.g., NS/O; baby hamster kidney (BHK) cell lines, e.g., ATCC CRL-1632 or ATCC CCL-10; and human cells, e.g., HEK 293 (ATCC CRL-1573). Additional suitable cell lines are known in the art and available from public depositories such as the American Type Culture Collection, Rockville, Md.

Nucleic Acid Copy Number and Levels of Expression

As shown in the examples that follow, the copy number of an exogenous nucleic acid expressing a thioesterase in a host affects cell viability, cell growth, vector stability in the host, and/or fatty acid product production.

Accordingly, in various versions of the invention the host includes no more than about 500, about 250, about 150, about 100, about 75, about 50, about 30, or about 25 copies of a nucleic acid encoding a thioesterase and/or ACC. Alternatively or in addition, the host in various versions of the invention includes no less than about 2, about 3, about 4, about 5, about 7, about 10, or about 15 copies of a nucleic acid encoding a thioesterase and/or ACC. Preferred versions include of from about 2 to about 250, more preferably of from about 3 to about 150, more preferably of from about 5 to about 100, and most preferably of from about 5 to about 30 copies of a nucleic acid encoding a thioesterase and/or ACC.

In some specific versions of the invention, the host includes no more than about 100, about 90, about 75, about 50, about 25, about 10, about 7, or about 5 copies of a nucleic acid encoding a thioesterase and/or ACC in the exponential phase of growth. Alternatively or in addition, the host in various versions of the invention includes no less than about 3, about 4, or about 5 copies of a nucleic acid encoding a thioesterase and/or ACC in the exponential phase of growth. Preferred versions include of from about 3 to about 30 or of from about 5 to about 25 copies of a nucleic acid encoding a thioesterase and/or ACC in the exponential phase of growth.

In some specific versions of the invention, the host includes no more than about 500, about 250, about 150, about 100, about 75, about 50, about 30, or about 20 copies of a nucleic acid encoding a thioesterase and/or ACC in the stationary phase of growth. Alternatively or in addition, the host in various versions of the invention includes no less than about 2, about 3, about 4, about 5, about 7, or about 10 copies of a nucleic acid encoding a thioesterase and/or ACC in the stationary phase of growth. Preferred versions include of from about 2 to about 250, more preferably of from about 10 to about 150, more preferably of from about 10 to about 100, more preferably of from about 10 to about 30 copies, and most preferably about 20 copies of a nucleic acid encoding a thioesterase and/or ACC in the stationary phase of growth.

The nucleic acid copy numbers described above are preferably employed with the $P_{BAD}$ promoter system induced at maximal levels or a promoter system having similar strength. Promoters having a similar strength to $P_{BAD}$ include the Ptet promoter, the prpBCDE promoter (PprpB), weak sigma70 promoters, and several promoters derived from engineered libraries (see Alper et al. (2005) *PNAS* 102 (36):12678-83). Higher nucleic acid copy numbers and/or stronger promoters may also be used, preferably in inducible or repressible promoter systems wherein the nucleic acid is expressed with a sub-saturating amount of effector. For an inducible promoter system, the nucleic acid is preferably expressed with an amount of an inducing effector of from about 0.25% to about 10%, of from about 0.5% to about 10%, of from about 1% to about 10%, of from about 2.5% to about 10%, or about 5% of the minimal saturating amount. For a repressible promoter system, the nucleic acid is preferably expressed with an amount of a repressible effector of from about 90% to about 99.75%, of from about 90% to about 99.5%, of from about 90% to about 99%, of from about 90% to about 97.5%, or about 95% of the minimal saturating amount. With such sub-saturating amounts of effector, the host may include about 50 or more copies of a nucleic acid encoding a thioesterase and/or ACC, such as about 100 or more copies, about 150 or more copies, about 200 or more copies, about 250 or more copies, about 300 or more copies or about 500 or more copies.

The requirements of nucleic acid copy number mentioned above refer to the average copy number measured in a population of cells. Therefore, a single cell comprising fewer than 5 copies of a particular nucleic acid, the single cell being in a population of cells that on average has more than 5 copies of the nucleic acid, does not fulfill the requirement of having no more than 5 copies of the nucleic acid.

The copy number of the nucleic acid or the vector comprising the nucleic acid in the host is a function, in part, of the origin of replication on the vector. Suitable origins of replication for use in the present invention include but are not limited to those derived from pBR322 or its derivatives (such as pTrc99A) (colE1 origin), pACYC or its derivatives (p15A origin), pBBR1 or its derivatives (pBBR1 origin), pSC101 or its derivatives (see Sugiura et al. (1993) *J. Bacteriol.* 175(18): 5993-6001), R1 plasmid or its derivatives, P1 plasmid or its derivatives, F plasmid or its derivatives (such as a mini-F plasmid), R6K plasmid or its derivatives, or RK2 plasmid or its derivatives. Preferred origins of replication include those derived from pACYC or its derivatives (p15A origin) or pBBR1 or its derivatives (pBBR1 origin). Methods for generating a vector with origins of replication derived from the above-mentioned sources as well as the copy numbers associated with each origin of replication are provided in the examples that follow.

Figure 3:
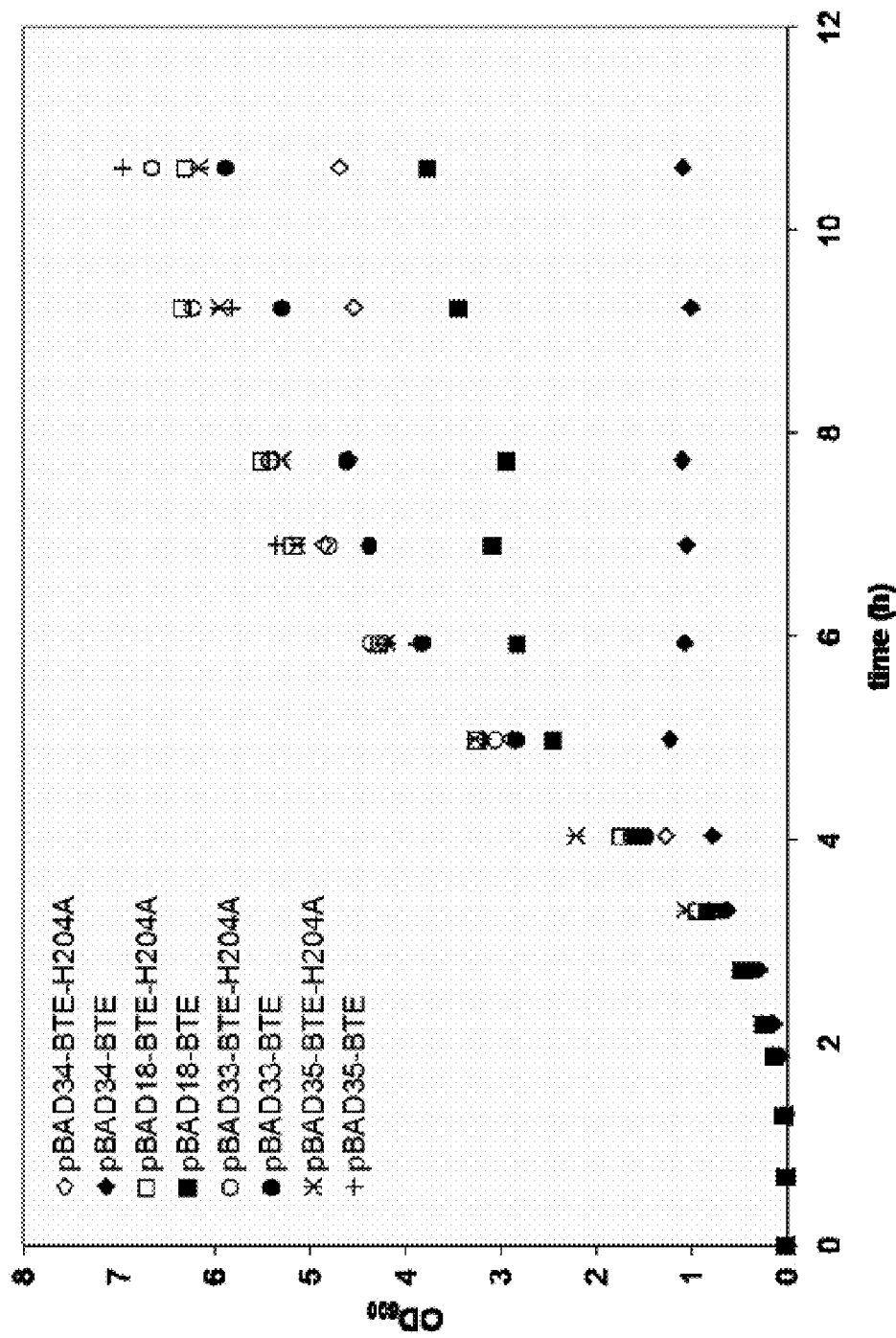
FIG. 3 depicts a time course of growth of *E. coli* cultures (strain RL08; see Table 2) harboring plasmids expressing BTE (filled markers) or non-functional BTE-H204A (open markers) monitored by optical density ($OD_{600}$). Cells were grown at 37° C. in shake flasks containing LB medium supplemented with 0.4% (v/v) glycerol and appropriate antibiotics for each vector. Cells were induced at an $OD_{600}$ of 0.2 by the addition of a final concentration of 0.2% (w/v) L-arabinose.

In some versions of the invention, the host is growth-competent. "Growth-competent" refers to the property of maintaining growth in culture with respect to a control. For example, a host comprising a nucleic acid expressing an enzyme is growth competent if it is capable of proliferating at a rate equal to a host comprising a nucleic acid expressing a non-functional version of the enzyme. Examples of growth-compenent hosts and non-growth-competent hosts are shown in FIG. 3. In preferred versions of the invention, the host is growth-competent at 37° C. (see examples that follow).

In some versions of the invention, the host is recombinantly stable. "Recombinantly stable" refers to the ability to retain an exogenous nucleic acid or vector comprising the nucleic acid over several generations in culture. The property of being recombinantly stable is typically a function of temperature, copy number of the nucleic acid in the host, the level of expression of the nucleic acid in the host, and/or the effect of the product expressed from the nucleic acid on the host. In preferred versions of the invention, the host is recombinantly stable at 37° C. (see examples that follow).

Carbon Chain Characteristics

Using the teachings provided herein, a range of products can be produced. These products include hydrocarbons, fatty alcohols, fatty acid esters, and waxes. Some of these products are useful as biofuels and specialty chemicals. These products can be designed and produced in microorganisms. The products can be produced such that they contain branch points, levels of saturation, and carbon chain length, thus making these products desirable starting materials for use in many applications.

The expression of heterologous FAS genes originating from different species or engineered variants can be introduced into the host to result in the biosynthesis of fatty acid metabolites structurally different (in length, branching, degree of unsaturation, etc.) than those of the native host. These heterologous gene products can also be chosen or engineered so that they are unaffected by the natural complex regulatory mechanisms in the host and, therefore, function in a manner that is more controllable for the production of the desired commercial product. For example, the FAS enzymes from *Bacillus subtilis, Saccharomyces cerevisiae, Streptomyces* spp, *Ralstonia, Rhodococcus, Corynebacteria, Brevibacteria, Mycobacteria*, oleaginous yeast, and the like can be expressed in the production host.

One of ordinary skill in the art will appreciate that when a production host is engineered to produce a fatty acid from the fatty acid biosynthetic pathway that contains a specific level of unsaturation, branching, or carbon chain length, the resulting engineered fatty acid can be used in the production of the fatty acid products. Hence, fatty acid derivatives generated from the production host can display the characteristics of the engineered fatty acid. For example, a production host can be engineered to make branched, short chain fatty acids, and then further engineered (i.e., by introducing alcohol-forming enzymes such as FAR) to produce branched, short chain fatty alcohols. Similarly, a hydrocarbon can be produced by engineering a production host to produce a fatty acid having a defined level of branching, unsaturation, and/or carbon chain length, thus producing a homogenous hydrocarbon population. Moreover, when an unsaturated alcohol, fatty acid ester, or hydrocarbon is desired, the fatty acid biosynthetic pathway can be engineered to produce low levels of saturated fatty acids, and an additional desaturase can be expressed to lessen the saturated product production. Methods for producing fatty acid derivatives having the above-mentioned characteristics are described in PCT application number PCT/US2007/011923 (WO 2007/136762), incorporated herein by reference.

Fermentation

The production and isolation of fatty acid products can be enhanced by employing specific fermentation techniques. One method for maximizing production while reducing costs is increasing the percentage of the carbon source that is converted to hydrocarbon products. During normal cellular lifecycles, carbon is used in cellular functions such as producing lipids, saccharides, proteins, organic acids, and nucleic acids. Reducing the amount of carbon necessary for growth-related activities can increase the efficiency of carbon source conversion to output. This can be achieved by first growing microorganisms to a desired density, such as a density achieved at the peak of the log phase of growth. At such a point, replication checkpoint genes can be harnessed to stop the growth of cells. Specifically, quorum sensing mechanisms (reviewed in Camilli and Bassler (2006) *Science* 311:1113; Venturi (2006) *FEMS Microbiol. Rev.* 30:274-291; and Reading and Sperandio (2006) *FEMS Microbiol. Lett.* 254:1-11) can be used to activate genes such as p53, p21, or other checkpoint genes. Genes that can be activated to stop cell replication and growth in *E. coli* include umuDC genes, the overexpression of which stops the progression from stationary phase to exponential growth (Murli et al. (2000) *J. of Bact.* 182:1127). UmuC is a DNA polymerase that can carry out translesion synthesis over non-coding lesions—the mechanistic basis of most UV and chemical mutagenesis. The umuDC gene products are used for the process of translesion synthesis and also serve as a DNA damage checkpoint. UmuDC gene products include UmuC, UmuD, umuD', $UmuD_2C$, $UmuD'_2$ and $UmUD_2$. Simultaneously, the product-producing genes would be activated, thus minimizing the need for replication and maintenance pathways to be used while the fatty acid product is being made.

The percentage of input carbons converted to hydrocarbon products is a cost driver. The more efficient the process is (i.e., the higher the percentage), the less expensive the process is. For oxygen-containing carbon sources (i.e., glucose and other carbohydrate based sources), the oxygen must be released in the form of carbon dioxide. For every two oxygen atoms released, a carbon atom is also released. The maximal theoretical metabolic efficiencies for fatty acid-derived products are about 34% (w/w) (i.e., about 0.3-0.35 g/g). This figure, however, changes for other hydrocarbon products and carbon sources. Typical efficiencies in the literature are between about 8-14%. Engineered microorganisms which produce hydrocarbon products can have greater than 1, 3, 5, 10, 15, 20, 25, and 30% efficiency. In one example, microorganisms will exhibit an efficiency of about 10% to about 25%. In other examples, such microorganisms will exhibit an efficiency of about 25% to about 30%, and in other examples, such microorganisms will exhibit >30% efficiency.

In some examples where the final product is released from the cell, a continuous process can be employed. In this approach, a reactor with organisms producing fatty acid products can be assembled in multiple ways. In one example, a portion of the media is removed and let to sit. Fatty acid products are separated from the aqueous layer, which will, in turn, be returned to the fermentation chamber.

In one example, the fermentation chamber will enclose a fermentation that is undergoing a continuous reduction. In this instance, a stable reductive environment is created. The electron balance would be maintained by the release of carbon dioxide (in gaseous form). Efforts to augment the $NAD^+$/NADH and $NADP^+$/NADPH balance can also facilitate in stabilizing the electron balance.

The availability of intracellular NADPH can be enhanced by engineering the production host to express an NADH:NADPH transhydrogenase. The expression of one or more NADH:NADPH transhydrogenases converts the NADH produced in glycolysis to NADPH which enhances the production of fatty acids.

Disclosed herein is a system for continuously producing and exporting fatty acid products out of recombinant host microorganisms via a transport protein. Many transport and efflux proteins serve to excrete a large variety of compounds and can be evolved to be selective for a particular type of fatty acid products. Thus, in some embodiments, an exogenous nucleic acid encoding an ABC transporter will be functionally expressed by the recombinant host microorganism, so that the microorganism exports the fatty acid product into the culture medium. In one example, the ABC transporter is an ABC transporter from *Caenorhabditis elegans, Arabidopsis thalania, Alkaligenes eutrophus*, or *Rhodococcus erythropolis* (locus AAN73268). In another example, the ABC transporter is an ABC transporter chosen from CER5 (locuses At1g51500 or AY734542), AtMRPS, AmiS2 and AtPGP1. In some examples, the ABC transporter is CER5. In yet another example, the CER5 gene is from *Arabidopsis* (locuses At1g51500, AY734542, At3g21090 and At1g51460).

The transport protein, for example, can also be an efflux protein selected from: AcrAB, TolC, MdtABC, EmrAB, AcrE, and AcrEF from *E. coli*, or tll1618, tll1619 and tll0139 from *Thermosynechococcus elongatus* BP-I.

In addition, the transport protein can be, for example, a fatty acid transport protein (FATP) selected from *Drosophila melanogaster, Caenorhabditis elegans, Mycobacterium tuberculosis*, or *Saccharomyces cerevisiae* or any one of the mammalian FATPs. The FATPs can additionally be resynthesized with the membranous regions reversed in order to invert the direction of substrate flow. Specifically, the sequences of amino acids composing the hydrophilic domains (or membrane domains) of the protein could be inverted while maintaining the same codons for each particular amino acid. The identification of these regions is well known in the art.

Production hosts can also be chosen for their endogenous ability to release fatty acid products. The efficiency of product production and release into the fermentation broth can be expressed as a ratio of intracellular product to extracellular product. In some examples the ratio can be 5:1, 4:1, 3:1, 2:1, 1:1, 1:2, 1:3, 1:4, or 1:5.

The production host can be additionally engineered to express recombinant cellulosomes, such as those described in PCT application number PCT/US2007/003736, which will allow the production host to use cellulosic material as a carbon source. For example, the production host can be additionally engineered to express invertases (EC 3.2.1.26) so that sucrose can be used as a carbon source.

Similarly, the production host can be engineered using the teachings described in U.S. Pat. Nos. 5,000,000, 5,028,539, 5,424,202, 5,482,846, and 5,602,030 to Ingram et al. so that the production host can assimilate carbon efficiently and use cellulosic materials as carbons sources.

Post-Production Processing

The fatty acid products produced during fermentation can be separated from the fermentation media. Any technique known for separating lipids from aqueous media can be used. One exemplary separation process provided herein is a two-phase (bi-phasic) separation process. This process involves fermenting the genetically engineered production hosts under conditions sufficient to produce a fatty acid, allowing the fatty acid to collect in a non-polar or organic phase and separating the non-polar phase from the aqueous fermentation broth. This method can be practiced in both batch and continuous fermentation settings.

Bi-phasic separation uses the relative immisiciblity of lipids to facilitate separation. "Immiscible" refers to the relative inability of a compound to dissolve in water and is defined by the compound's partition coefficient. The partition coefficient, P, is defined as the equilibrium concentration of the compound in a non-polar phase divided by the concentration at equilibrium in an aqueous phase (i.e., fermentation broth). In a bi-phasic system, the non-polar phase is usually the phase formed by the fatty acid product during the production process. However, in some examples, a non-polar phase can be provided (such as a layer of octane to facilitate product separation). When describing a two phase system, the P is usually discussed in terms of logP. A compound with a logP of 10 would partition 10:1 to the non-polar phase, while a compound of logP of 0.1 would partition 10:1 to the aqueous phase. One of ordinary skill in the art will appreciate that by choosing a fermentation broth and the non-polar phase such that the fatty acid product being produced has a high logP value, the fatty acid product will separate into the non-polar phase, even at very low concentrations in the fermentation vessel.

The fatty acid product produced by the methods described herein will be relatively immiscible in the fermentation broth, as well as in the cytoplasm. Therefore, the fatty acid product will collect in the non-polar phase. The collection of the products in the non-polar phase will lessen the impact of the fatty acid product on cellular function and will allow the production host to produce more product.

The fatty acids, fatty alcohols, fatty acid esters, waxes, and/or hydrocarbons produced as described herein allow for the production of homogeneous compounds wherein at least 60%, 70%, 80%, 90%, or 95% of the fatty acid product produced will have carbon chain lengths that vary by less than 4 carbons, or less than 2 carbons. These compounds can also be produced so that they have a relatively uniform degree of saturation. For example, at least 60%, 70%, 80%, 90%, or 95% of the fatty acids, fatty alcohols, fatty acid esters, hydrocarbons, and waxes will be mono-, di-, or tri-unsaturated. These compounds can be used directly as fuels, personal care additives, or nutritional supplements. These compounds can also be used as feedstock for subsequent reactions such as transesterification; hydrogenation; catalytic cracking via hydrogenation, pyrolisis, or both; or epoxidation reactions to make other products.

Decarboxylation

In a preferred version of the invention, the fatty acid product produced by the cell and purified from the fermentation broth is a fatty acid, and the fatty acid is modified post-purification into a hydrocarbon by decarboxylation. Methods of decarboxylating a fatty acid include but are not limited to putative enzymatic decarboxylation (Banerjee et al. (2002) *Critical Reviews in Biotechnology*, 22:245-279) and catalytic decarboxylation (Maki-Arvela et al. (2007) *Energy & Fuels*, 21: 30-41; U.S. Pat. Pub. 2007/0244343). A preferred method of decarboxylating a fatty acid is by catalysis such as palladium-on-carbon (Pd/C) catalysis (Maki-Arvela et al. (2008) *Fuel*, 87 (17-18): 3543-3549). In addition to decarboxylating the fatty acid, the Pd/C catalyst fully hydrogenates the fatty acid, generating an alkane. Fatty acid derivatives may also be decarboxylated using the above methods.

The fatty acids can also be converted to other useful liquid fuels by enzymatic or catalytic esterification (see Kalscheuer et al. (2006) *Microbiology*, 152, 2529-36; see also Schirmer et al. (2010) *Science*, 329 (5991):559-62).

Fuel Compositions

The fatty acid products or secondary products described herein can be used as fuel. One of ordinary skill in the art will appreciate that depending upon the intended purpose of the fuel, different fatty acid products or secondary products can be produced and used. For example, for automobile fuel that is intended to be used in cold climates, a branched fatty acid product or secondary product may be desirable. Using the teachings provided herein, branched hydrocarbons, fatty acid esters, and alcohols can be made. Using the methods described herein fuels comprising relatively homogeneous fatty acid products or secondary products that have desired fuel qualities can also be produced. The preferred product or secondary product described herein for use as a fuel includes medium- to long-chain alkanes for use as diesel fuel. The fatty acid product-based fuels can be combined with other fuels or fuel additives to produce fuels having desired properties.

Systems for Fatty Acid Product Production

Figure 9:
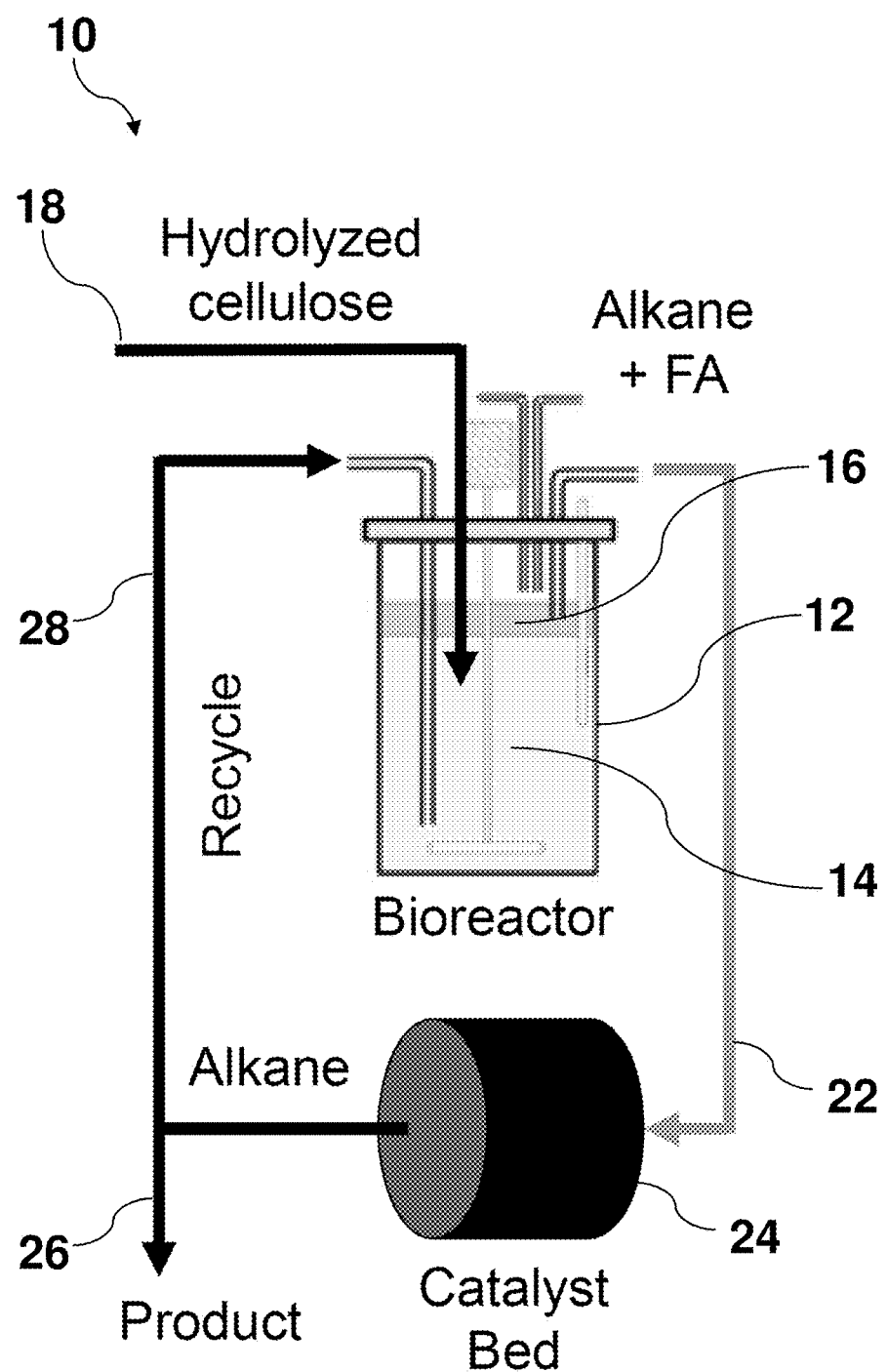
FIG. 9 depicts a schema for a continuous-flow system of the present invention for fermenting hosts in a bioreactor, purifying fatty acid products from the hosts, modifying the purified fatty acid products into secondary products, yielding a first portion of the secondary product, and recycling a second portion of the secondary product to the bioreactor.

A system 10 for fuel production using the methods and tools described herein is shown in FIG. 9. The system 10 includes a bioreactor 12 that includes a fermentation broth as a first phase 14 and a non-polar solvent, such as an alkane, as a second phase 16. Hosts such as the genetically modified microorganisms described herein are cultured in the fermentation broth 14 under conditions that permit product production. A carbon source 18 is added to the fermentation broth 14 to support the hosts. In the exemplary version, the carbon source 18 is hydrolyzed cellulose. The carbon source 18 is added to the fermentation broth 14 at a rate equaling its consumption. Fatty acid products 20 produced by the hosts, such as fatty acids, are purified from the fermentation broth 14 by partitioning to the second phase 16. The fatty acid product-second phase mixture is collected as a product stream 22 and fed through a chemical modifier 24 such as a catalyst bed to modify the fatty acid product to generate a secondary product. In a preferred version, the chemical modifier 24 is a Pd/C catalyst bed, and the product is decarboxylated into an alkane. A first portion of the secondary product is collected via a final product stream 26. A second portion of the secondary product is recycled via a recycling stream 28 to the bioreactor to serve as a continuous source of the second phase 16. Thus, in the preferred version, the second phase 16 comprises or fully consists of the chemical entity that is the secondary product. The schema shown in FIG. 9 is not limited to the specific entities described herein. For example, it can be used for any carbon source 18, fermentation broth/first phase 14, second phase 16, fatty acid product, chemical modifier 24, and secondary product.

EXAMPLES

Introduction

Medium and long chain hydrocarbons can potentially serve as replacements for diesel, rendering them an attractive target for microbial production from lignocellulosic feedstocks. Microbially synthesized fatty acids are logical precursors to diesel-like hydrocarbons, and offer the flexibility to exploit a variety of biomass-derived carbon sources. Fatty acid biosynthesis (FIG. 1) is initiated by the conversion of acetyl-coenzyme A (CoA) to malonyl-CoA by acetyl-CoA carboxylase (ACC). Fatty acid biosynthesis is highly regulated at this initial rate-limiting step (Davis et al., (2000) *J. Biol. Chem.* 275:28593-28598; Li et al., (1993) *J. Bacteriol* 175:332-340). From malonyl-CoA, the condensing intermediate malonyl-acyl carrier protein (ACP), and ultimately the initial species that enters the elongation cycle, acetoacetyl-ACP, are generated. The elongation cycle fully reduces the β-ketoacyl-ACP to an acyl-ACP, which is then condensed with malonyl-ACP to lengthen the fatty acid molecule. Long chain length acyl-ACPs are substrates for two acyltransferases, PlsB and PlsC, as part of phospholipid biosynthesis. The accumulation of acyl-ACPs feedback inhibits multiple enzymes in fatty acid biosynthesis, representing one mode of coordination of lipid production to the growth rate (Davis et al., (2001) *J. Bacteriol* 183:1499-1503; Heath et al. (1996) *J. Biol. Chem.* 271:1833-1836). The most dramatic examples of decoupling fatty acid biosynthesis from normal modes of regulation come from the heterologous expression of plant acyl-ACP thioesterases. While several have been expressed in *E. coli* (Yuan et al., (1995) *Proc. Natl. Acad. Sci. USA* 92:10639-10643; Serrano-Vega et al., (2005) *Planta* 221: 868-880; Jha et al., (2006) *Plant Physiol. Biochem.* 44:645-655; Ghosh et al., (2007) *Plant Physiol. Biochem.* 45:887-897), the FatB-type medium chain acyl-ACP thioesterase from *Californica umbellularia* demonstrated the largest increase in total fatty acid production, with a chain length distribution heavily skewed toward $C_{12}$ and $C_{14}$ species (Voelker et al. (1994) *J. Bacteriol* 176:7320-7327). However, expression of the *Californica umbellularia* thioesterase in *E. coli* in the conventional manner adversely affects growth of the transformed cells at 30° C., which is even more severe at 37° C. (Voelker 1994). Plasmid curing also occurs at 37° C. The adverse affect of the *Californica umbellularia* thioesterase in *E. coli* on growth and plasmid stability in conventional systems hinders the large-scale production of lipid.

In this study, we sought to further understand previously reported instabilities of plasmids expressing the *U. californica* acyl-ACP thioesterase (BTE) (Voelker 1994) by varying the copy number of a codon-optimized version of the gene on plasmids having different origins of replication. Previous studies expressing acyl-ACP thioesterases in *E. coli* have been conducted at 30° C. due to this putative instability (Lu et al., (2008) *Biotechnol. Bioeng.* 94:151-158; Feng et al., (2009) *J. Biol. Chem.* 284:29526-29535). However, no additional studies have been conducted to determine any rationale for this instability. As described herein, *E. coli* was engineered to overproduce free fatty acids via several modifications: (1) expression of a codon-optimized acyl-ACP thioesterase from *U. californica* (BTE) on a suitable plasmid; (2) deletion of the fadD gene encoding acyl-CoA synthetase, the first enzyme involved in β-oxidation; and/or (3) overexpression of ACC.

Materials and Methods

Strain Construction: Bacterial strains, plasmids, and oligonucleotide primers used in this study are listed in Tables 2 and 3. Oligonucleotide primers were purchased from Integrated DNA Technologies, Inc. (Coralville, Iowa). Chemicals and reagents were purchased from Fisher Scientific (Pittsburgh, Pa.) unless otherwise specified. *E. coli* K-12 MG1655 was obtained from the *E. coli* Genetic Stock Center (New Haven, Conn.) and was the background strain used in this work. Strain RL01 was constructed by deleting the fadD gene from the MG1655 chromosome by λ Red-mediated recombination (Datsenko et al., (2000) *Proc. Natl. Acad. Sci. USA* 97:6640-6645) using the λ Red recombinase encoded on plasmid pKD46. Plasmid pKD13 was used as the template for amplification of the linear cassette using primers 1 and 2. The kan cassette was removed by expressing the FLP recombinase encoded on plasmid pCP20. Strain NRD204 (K-12 MG1655 araBAD::cat) (De Lay et al., (2007) *J. Biol. Chem.* 282: 20319-20328) was generously donated by Dr. Cronan (University of Illinois at Urbana-Champaign). Strain RL08 was constructed by P1 phage transduction (Thomason et al., (2007) *Curr. Protoc. Mol. Biol.* 1:17) of the araBAD::cat insertion into strain RL01 via a modified protocol utilizing selective plates containing 1.25 mM sodium pyrophosphate as a calcium chelator. The cat cassette was removed using pCP20. To minimize the possible presence of multiple insertions by λ Red recombination, all recombinant strains were used as donors to transduce back into the parent strain. Gene insertions and deletions were verified by colony PCR using primers 3 and 4 for fadD and 5 and 6 for araBAD, and by the absence of growth after plating on M9 agar supplemented with either 0.1% (w/v) sodium oleate (TCI America) as previously described (Overath et al., (1969) *Eur. J. Biochem.* 7:559-574), or 0.4% (w/v) L-arabinose (Calbiochem, San Diego, Calif.) as carbon sources.

TABLE 2

Bacterial Strains and plasmids used in this study.

| Strain/plasmid | Relevant genotype/property[a] | Source or reference |
|---|---|---|
| Strains (*Escherichia coli*) | | |
| K-12 MG1655 | F− λ− ilvG− rfb-50 rph-1 | CGSC |
| RL01 | K-12 MG1655 fadD::kan | This report |
| RL02 | K-12 MG1655 ΔfadD | This report |

TABLE 2-continued

Bacterial Strains and plasmids used in this study.

| Strain/plasmid | Relevant genotype/property[a] | Source or reference |
|---|---|---|
| NRD204 | K-12 MG1655 araBAD::cat | DeLay and Cronan, 2007 |
| RL07 | K-12 MG1655 ΔfadD araBAD::cat | This report |
| RL08 | K-12 MG1655 ΔfadD ΔaraBAD | This report |
| DH10B | F− mcrA Δ(mrr-hsdRMS-mcrBC) φ80lacZΔM15 ΔlacX14 recA1 endA1 araD139 Δ(ara, leu)7697 galU galK λ− rpsL, nupG | Invitrogen |
| Plasmids | | |
| pKD13 | template plasmid, R6K gamma origin, Amp$^R$, Kan$^R$ | Datsenko and Wanner, 2000 |
| pKD46 | carries Red recombinase under P$_{araB}$ control, R101 origin, repA101(ts), Amp$^R$ | Datsenko and Wanner, 2000 |
| pCP20 | carries yeast FLP recombinase under constitutive promoter, pSC101 origin, λ cI857+, λ p$_R$ Rep$^{ts}$, Amp$^R$, Cm$^R$ | Cherepanov & Wackernagel, 1995 |
| pBAD33 | P$_{BAD}$ promoter, pACYC origin, Cm$^R$ | Guzman et al., 1995 |
| pBAD18 | P$_{BAD}$ promoter, pBR322 origin, Amp$^R$ | Guzman et al., 1995 |
| pBAD24 | P$_{BAD}$ promoter, pBR322 origin, Amp$^R$ | Guzman et al., 1995 |
| pRL1 | pBAD33 carrying accD under P$_{BAD}$ control, Cm$^R$ | This report |
| pRL2 | pRL1 carrying accDA under P$_{BAD}$ control, Cm$^R$ | This report |
| pBAD33-ACC | pRL2 carrying accDABC under P$_{BAD}$ control, Cm$^R$ | This report |
| pBAD18-BTE | pBAD18 carrying BTE under P$_{BAD}$ control, Amp$^R$ | This report |
| pBAD18-BTE-H204A | pBAD18 carrying BTE with H204A under P$_{BAD}$ control, Amp$^R$ | This report |
| pBT-2 | pBBR1-MCS origin, Kan$^R$ | Lynch and Gill, 2006 |
| pUC19 | pUC origin, lacZα, Amp$^R$ | New England Biolabs |
| pBAD34 | P$_{BAD}$ promoter, pUC origin, Amp$^R$ | This report |
| pBAD34-BTE | pBAD34 carrying BTE under P$_{BAD}$ control, Amp$^R$ | This report |
| pBAD34-BTE-H204A | pBAD34 carrying BTE-H204A under P$_{BAD}$ control, Amp$^R$ | This report |
| pBAD35 | pBT-2 containing araC-P$_{BAD}$-MCS-rrnB fragment from pBAD18, Kan$^R$ | This report |
| pBAD35-BTE | pBAD35 carrying BTE under P$_{BAD}$ control, Kan$^R$ | This report |
| pBAD35-BTE-H204A | pBAD35 carrying BTE-H204A under P$_{BAD}$ control, Kan$^R$ | This report |

[a]Abbreviations: Amp, ampicillin; Cm, chloramphenicol; Kan, kanamycin; R, resistance; ts, temperature sensitive.

TABLE 3

Oligonucleotide primers used in this study.

| | Primer name | Sequence (5' to 3')[a] | SEQ ID NO: |
|---|---|---|---|
| 1 | fadDKO_fwd | GGTTGCGATGACGACGAACACGCATTTTAGAGGTGAAG AAGTGTAGGCTGGAGCTGCTTC | 3 |
| 2 | fadDKO_rev | CGCCGGATTAACCGGCGTCTGACGACTGACTTAACGCT CAATTCCGGGGATCCGTCGACC | 4 |
| 3 | fadDKO_colPCR_fwd | ACGGCATGTATATCATTTGGG | 5 |
| 4 | fadDKO_colPCR_rev | CTTTAGTGGGCGTCAAAAAAAC | 6 |
| 5 | araBADKO_colPCR_fwd | AAGCGGGACCAAAGCCATGAC | 7 |
| 6 | araBADKO_colPCR_rev | AGGAGACTTCTGTCCCTTGCG | 8 |
| 7 | accD_fwd | CCCGAGCTCAGGTCCCTAATGAGCTGGATTGAAC | 9 |
| 8 | accD_rev | CCCCCCGGGTCAGGCCTCAGGTTCCTGATCC | 10 |
| 9 | accA_fwd | GGGCCCGGGAGGAATACTATGAGTCTGAATTTCCTTG | 11 |
| 10 | accA_rev | GGGGTCGACCTCGAGTTTACGCGTAACCGTAGCTCATC | 12 |
| 11 | accBC_fwd | CCCCTCGAGACGGAACCCACTCATGGATATTC | 13 |
| 12 | accBC_rev | CCCGCATGCTTATTTTTCCTGAAGACCGAGTTTTTC | 14 |

TABLE 3-continued

Oligonucleotide primers used in this study.

| Primer name | Sequence (5' to 3')[a] | SEQ ID NO: |
|---|---|---|
| 13 BTE-H204A_mega_rev | TCTCATCCGCCAAAAC | 15 |
| 14 BTE-H204A_mega_mut | TGTTAATCAGGCTGTGAACAACCTGAAATACG | 16 |
| 15 BTE-H204A_mega_fwd | TTGGGCTAGCGAATTC | 17 |
| 16 pBAD18-to-pBT_fwd | TTATGACAACTTGACGGCTACATC | 18 |
| 17 pBAD18-to-pBT_rev | AGAGTTTGTAGAAACGCAAAAAGGC | 19 |
| 18 BTE-to-pBAD35_fwd | ACGCTTTTTATCGCAACTCTC | 20 |
| 19 BTE-to-pBAD35_rev | GGG<u>GCATGC</u>TTAAACACGAGGTTCGCGC | 21 |
| 20 pBAD33ara_fwd | GGG<u>CTCGAG</u>TTATGACAACTTGACGGCTACATC | 22 |
| 21 pBAD33ara_rev | GGG<u>AGATCT</u>AGAGTTTGTAGAAACGCAAAAAGGC | 23 |
| 22 pUC19ara_fwd | GGG<u>CTCGAG</u>GTGCCTAATGAGTGAGCTAACTC | 24 |
| 23 pUC19ara_rev | GGG<u>AGATCT</u>TAGTTAAGCCAGCCCCGACAC | 25 |
| 24 qPCR_BTE_fwd | CTGTCTACCATCCCGGAC | 26 |
| 25 qPCR_BTE_rev | TCAGTTTTTGCAGTTTCTTGATTTCG | 27 |
| 26 qPCR_ompA_fwd | TGTTGAGTACGCGATCACTC | 28 |
| 27 qPCR_ompA_rev | GTTGTCCGGACGAGTGC | 29 |

[a]Restriction sites are underlined.

Gene Synthesis: The 897-bp portion of the DNA sequence of BTE lacking the 83 amino acids at the N-terminus that appear to be involved in thylakoid targeting (Voelker et al., (1992) *Science* 257:72-74 and containing the XbaI site formerly used to clone a functional part of the gene in *E. coli* (Ohlrogge et al., (1995) *Arch. Biochem. Biophys.* 317:185-190) was codon-optimized for expression in *E. coli*, with common restriction sites eliminated. An artificial ribosome binding site, a spacer sequence, a start codon, and bases to create an in-frame sequence were added upstream of the gene fragment. The full sequence (FIG. 3) was custom-synthesized (Integrated DNA Technologies, Inc.) and was received in plasmid pUC57 (pUC57-BTE).

Plasmid Construction All cloning was performed in *E. coli* DH10B cells (Invitrogen, Carlsbad, Calif.), and all enzymes for cloning were purchased from New England Biolabs (Ipswich, Mass.). The accD gene encoding the β subunit of acetyl-CoA carboxyltransferase, the accA gene encoding the α subunit of acetyl-CoA carboxyltransferase, and the accBC operon encoding biotin carboxyl carrier protein and biotin carboxylase were amplified by PCR from MG1655 genomic DNA with their putative upstream ribosome binding sites (RBS) using primers 7 and 8, 9 and 10, and 11 and 12, respectively. These PCR products were sequentially inserted into pBAD33 (Guzman et al., (1995) *J. Bacteriol.* 177:4121-4130) between the SacI and XmaI sites (pRL1), SalI and XbaI sites (pRL2), and SphI and XhoI sites to create the artificial operon accDABC in plasmid pBAD33-ACC.

The BTE fragment from plasmid pUC57-BTE between the XmaI and HindIII sites was inserted into plasmid pBAD18 (Guzman et al., 1995) to generate plasmid pBAD18-BTE. To create a non-functional BTE for use as a negative control, a catalytic histidine at amino acid 204 was identified based on prior alignments of BTE with other plant acyl-ACP thioesterases (Yuan et al., 1996). A two-step megaprimer PCR procedure (Xu et al., (2003) *Mol. Bio.* 235:203-207) was used to mutagenize the first two nucleotides of the histidine codon at position 204 to create an alanine codon. Primers 13 and 14 were used in the first reaction to generate a 3' megaprimer from pBAD18-BTE template. This purified megaprimer and primer 15 were used to generate the complete BTE-H204A fragment, which was inserted as described for BTE to form plasmid pBAD18-BTE-H204A.

To generate another vector harboring the $P_{BAD}$ promoter system, the 1697-bp fragment between the start of the araC gene and the end of the rrnB terminator was amplified from pBAD18 (Guzman et al., 1995) with primers 16 and 17. This insert was treated with T4 polynucleotide kinase and blunt ligated into EcoRV-digested plasmid pBT-2 (Lynch et al., (2006) *Biotechnol. Bioeng.* 94:151-158) to form plasmid pBAD35. A fragment containing the BTE gene was amplified from pBAD18-BTE using primers 18 and 19 and inserted into pBAD35 between the XmaI and SphI sites to generate plasmid pBAD35-BTE. The same procedure was performed using pBAD18-BTE-H204A as a template to form plasmid pBAD35-BTE-H204A.

To generate a yet another vector harboring the $P_{BAD}$ promoter system, the 1693-bp fragment between the start of the araC gene and the end of the rrnB terminator was amplified from pBAD33 with primers 20 and 21. The 2284-bp fragment of pUC19 (New England Biolabs) containing the origin and Amp$^R$ marker was amplified with primers 22 and 23. These two fragments were digested with XhoI and BglII and ligated to form plasmid pBAD34. The XmaI/HindIII fragments containing BTE or BTE-H204A from pBAD18-BTE and pBAD18-BTE-H204A were inserted into pBAD34 to form plasmids pBAD34-BTE and pBAD34-BTE-H204A. All plasmid constructs described above were verified by sequencing.

Cell Transformation, Media, and Growth: Plasmids were electroporated into strain RL08 and selected on Luria-Bertani (LB) agar (Becton Dickinson, Cockeysville, Md.) containing 25 µg/mL kanamycin (pBAD35 constructs) or 50 µg/mL ampicillin (pBAD18 constructs) and 34 µg/mL chloramphenicol. All cultures were grown in a 37° C. shaker at 250 rpm. Overnight cultures inoculated from single colonies were used to inoculate shake flasks containing LB medium (Becton Dickinson) supplemented with 0.4% glycerol and antibiotics. The cultures were induced at an $OD_{600}$ of 0.2 with 0.2% (w/v) L-arabinose. This level of L-arabinose is known in the art to induce a maximal level of expression with the pBAD vector system. Samples of cell culture (2.5 mL) were taken for fatty acid analysis at indicated times.

Generation of Chromosomal Integrants: The DNA cassettes consisting of the BTE gene or H204A mutant thereof, $P_{BAD}$ promoter, araC gene, and rrnb terminator used to generate the vectors as described above were also used to construct chromosomal integrants with strain K-12 MG1655 ΔaraBAD via λ-red mediated recombination to disrupt the fadD gene (Datsenko et al., 2000).

Quantitative PCR for Determination of Copy Number: During early exponential phase (immediately prior to induction at OD 0.2) and early stationary phase (7.7 h after inoculation), 1 mL of cell culture was collected and centrifuged at 16,000×g for 1 minute. The cell pellet was resuspended in 100 µL of deionized water. One microliter of resuspended cell pellet was used directly as the template in a qPCR reaction with Maxima™ SYBR green/fluorescein qPCR master mix (Fermentas, Glen Burnie, Md.). Primers 24 and 25 were used for BTE amplification, and primers 26 and 27 for chromosomal ompA amplification. SYBR Green fluorescence was monitored with a Bio-Rad CFX96 optical reaction module (Bio-Rad, Hercules, Calif.). Threshold cycle ($C_t$) values were calculated by Bio-Rad CFX Manager software.

Fatty Acid Extraction and Methylation: To 2.5 mL samples of cell culture (three replicates for each culture at each sampling time), 5 µL of 10 mg/mL heptadecanoic acid (Fluka, Buchs, Switzerland) dissolved in ethanol and 50 µL of 10 mg/mL pentadecanoic acid (Acros Organics, Geel, Belgium) dissolved in ethanol were added as internal standards. Next, 100 µL of glacial acetic acid and 5.0 mL of a 1:1 (v/v) chloroform/methanol mixture were added (Bligh et al., (1959) Can. J. Biochem. Physiol. 37:911-917). The samples were inverted several times, vortexed vigorously, and centrifuged. The aqueous layer and cell debris were removed by aspiration, and the chloroform layer was stored at −80° C. until further processing. To methylate the fatty acids, the chloroform layer was thawed and evaporated under a nitrogen stream. Residual water was removed by lyophilization for approximately 1 hour. To the dried residue, 0.5 mL of 1.25 M HCl in methanol (Fluka) was added, and the reaction was incubated overnight (14 to 16 hours) at 50° C. The reaction mixtures were quenched by the addition of 5 mL of 100 mg/mL aqueous $NaHCO_3$ (Sigma-Aldrich Corp., St. Louis, Mo.), and fatty acid methyl esters were extracted twice into 0.5 mL hexane. The hexane layers were collected for analysis.

Gas Chromatography/Mass Spectrometry of Fatty Acid Methyl Esters: Gas chromatography/mass spectrometry (GC/MS) analysis was performed on a model 7890 Agilent GC (Agilent Technologies, Inc., Santa Clara, Calif.) with a 30 m×0.25 mm DB-5 capillary column (Agilent Technologies) and a model 5973N mass spectrometer. The oven temperature program was 100° C. for 2 min, 150° C. for 4 min, and a ramp to 250° C. at a rate of 4° C./min. One microliter of sample was injected with a 1:10 split ratio. Peak identification was achieved by comparison to internal standards and to the NIST Mass Spectral Database. Quantification was achieved by comparison of integrated peaks to calibration curves of a fatty acid methyl ester standard (Supelco No. 18918) with added methyl heptadecanoate (Fluka) and methyl pentadecanoate (Fluka). Due to the high concentration of dodecanoic acid in BTE-expressing cultures, 20-fold dilutions were injected to accurately quantify this species. Concentrations of decenoic, dodecenoic, and tetradecenoic methyl esters were estimated using the sensitivity ratio of hexadecenoic to hexadecanoic methyl esters in the external standard. Calculated sample concentrations were normalized to the recovered concentrations of internal standards and averaged for all replicates.

Decane Extraction of Fatty Acids: After 34 hours, 40 mL of decane (Acros Organics) was added to approximately 410 mL of each culture, and the mixtures were placed in a shaker at 250 rpm for 30 minutes. The resulting emulsions were acidified to facilitate phase separation by the addition of 10 mL of concentrated hydrochloric acid, shaken for one minute, and centrifuged at 2,500×g for 20 minutes or 16,000×g for 10 minutes. The decane layer was collected for catalytic conversion.

Catalytic Decarboxylation: The extracted fatty acids dissolved in decane were decarboxylated to alkanes over a 1 weight percent Pd/C catalyst (Sigma-Aldrich) in a plug flow reactor. The catalyst (1.1 g) was loaded into in a 0.25 inch tubular stainless steel reactor operating in an upflow configuration surrounded by aluminum blocks heated externally by a well-insulated furnace. The catalyst bed was held in place by plugs of quartz wool at the reactor entrance and exit. Prior to reaction, fresh catalyst was reduced in flowing $H_2$ (250 $cm^3$ (STP)/min at 300° C. (5° C./min ramp) for 4 h). The temperature was maintained at 300° C. and the pressure was maintained at 12 bar for reaction experiments. A liquid solution containing the fatty acids in the decane extraction was introduced (0.05 mL/min) into the upflow reactor using an HPLC pump along with a 5 percent $H_2$ co-feed flow of 250 $cm^3$ (STP)/min. The effluent liquid was collected at room temperature in a gas-liquid separator (Penberthy, Prophetstown, Ill.) and drained for GC/MS analysis (Shimadzu GC-2010; Shimadzu, Kyoto, Japan; with a mass spectrometer and DB-5 ms column from Alltech Deerfield, Ill.). Alkane concentrations were quantified by comparison to external standards containing undecane, dodecane, pentadecane, and hexadecane in a decane solvent. The tridecane peak was identified by its mass spectrum and its concentration was determined using an estimated response factor. A small quantity of undecane (2 µmol/mL) was present as an impurity in the decane received from the manufacturer. This concentration was subtracted from all undecane concentrations of converted culture extractions to yield the reported concentrations.

Results and Discussion

Initial Strain Construction and Optimization of BTE Copy Number: The development of an initial fatty acid overproducing strain followed the metabolic engineering strategy presented in FIG. 1. First, to prevent catabolism of free fatty acids, the gene encoding acyl-CoA synthetase (fadD) was deleted from the chromosome. Second, to prevent consumption of the inducing agent L-arabinose, the araBAD operon was deleted. This operon encodes three genes involved in the initial steps of L-arabinose degradation: L-ribulokinase, L-arabinose isomerase, and L-ribulose-5-phosphate 4-epimerase. The resulting strain, K-12 MG1655 ΔfadD ΔaraBAD, is designated strain RL08. Finally, to hydrolyze free fatty acids from acyl-ACP, a codon-optimized plant acyl-ACP thioesterase (BTE) from Umbellularia californica (FIG. 2) was cloned into various arabinose-inducible plasmids and transformed into strain RL08. The four selected plasmids were pBAD34 (pUC origin), pBAD18 (pBR322 origin without rop), pBAD33 (pACYC origin), and pBAD35 (pBBR1 origin). These plasmids are reported to range from highest to lowest copy number in the following order: the pUC origin (pBAD34) (Yanisch-Perron et al., (1985) *Gene* 33:103-119); pBAD18 (Guzman et al., 1995; Cronan, (2006) *Plasmid.* 55:152-157); and pBAD33 (Guzman et al., 1995; Chang et al., (1978) *J. Bacteriol.* 134:1141-1156). The only reported copy number of the pBBR1 origin in *E. coli* is 30 to 40 copies per cell (Antoine et. al., (1992) *Mol. Microbiol.* 6:1785-1799). An identical set of plasmids expressing a non-functional version of BTE with histidine-204 mutagenized to an alanine were also transformed into strain RL08 to serve as negative controls. Chromosomal integrants of the BTE and BTE-H204A cassettes were also constructed.

To determine preferred copy numbers for expressing BTE, cultures of strain RL08 harboring each plasmid or chromosomal insert (with both functional and non-functional BTE) were grown in shake flasks containing 50 mL of LB medium supplemented with 0.4% (v/v) glycerol. The $OD_{600}$ was monitored for growth (FIG. 3), and relative copy numbers of each plasmid were determined by quantitative PCR from cell cultures immediately before induction of transcription at OD 0.2, and during early stationary phase after an elapsed time of 7.7 hours from inoculation (Table 4). All experiments were performed at 37° C., and 0.2% L-arabinose was used to induce maximal expression from each plasmid vector.

Dramatically lower cell densities were observed after approximately 5 hours when BTE was expressed on plasmids pBAD34 and pBAD18 (FIG. 3). Expression of plasmids pBAD33-BTE and pBAD35-BTE did not exhibit reduced cell densities, which is notable at the 37° C. growth temperature. Non-functional BTE-H204A also did not exhibit similarly reduced cell densities, strongly suggesting that the decreased cell densities were due to thioesterase activity.

Figure 4:
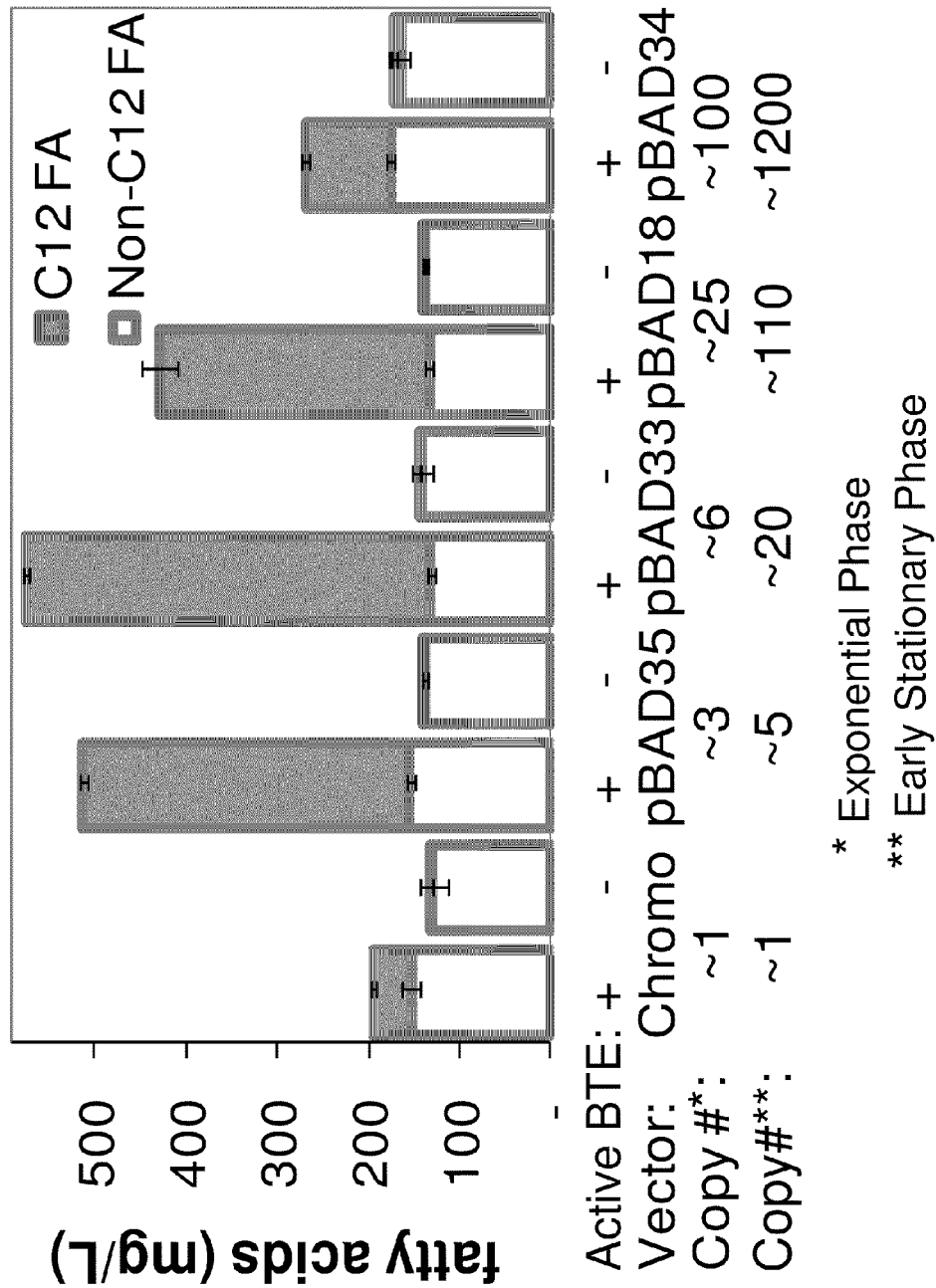
FIG. 4 depicts total fatty acid titers (µg/mL culture medium, open bars) and $C_{12}$ chain length fatty acid titers (saturated and estimated unsaturated, filled bars) extracted from *E. coli* RL08 cultures harboring plasmids expressing BTE (left-hand bars for each construct) or non-functional BTE-H204A (right-hand bars for each construct) or harboring chromosomal inserts of same at approximately 23 h post-inoculation. Error bars represent standard deviations about the mean of two or three replicate samples for either $C_{12}$ fatty acids (lower bars) or total fatty acids including $C_{12}$ (upper bars).

Relative copy numbers trended as expected (Table 4 and FIG. 4). Chromosomal insertion produces one copy per chromosome. The pBAD34 plasmid exhibited the highest number of copies per copy of the selected chromosomal internal standard, ompA, during pre-induction exponential growth and early stationary phase. The poorly characterized pBBR1 origin (present in pBAD35) is shown here to be present at the lowest copy number (~5) among the plasmids, similar to that of the pACYC origin during exponential growth. As expected, the pBAD18 construct was shown to have an intermediate copy number between that of pBAD35 and pBAD34. Similarly, pBAD33 during stationary phase had an intermediate copy number between that of pBAD35 and pBAD34. BTE copy numbers relative to ompA increased in early stationary phase for all vectors except pBAD35, which showed no change. This is likely due to the presence of multiple replication forks on the chromosome during rapid growth (Nordstrom et. al., (2006) *EMBO Rep.* 7:484-489), or the onset of nutrient limitations in the medium that stop replication from oriC while replication continues from many plasmid origins (Friehs, (2004) *Adv. Biochem. Eng. Biotechnol.* 86:47-82). The plasmids expressing BTE-H204A all displayed lower copy numbers during stationary phase than the corresponding plasmids expressing BTE, possibly as a result of increased cell lysis in these induced cultures. Variation in the lysis of whole cell templates has been previously implicated as a source of error in determining plasmid copy numbers by quantitative PCR (Providenti et al., (2006) *J. Microbiol. Methods* 65:476-487). Consistent with this hypothesis, no discrepancy in copy number was observed between plasmids harboring BTE and BTE-H204A during exponential growth prior to induction.

TABLE 4

Calculated copy numbers of BTE per copy of chromosomal gene ompA and fatty acid titers from cultures of strain RL08 harboring BTE.*

| BTE or BTE-H204 Vector | Copy number (per ompA) | | Fatty acid titer (% $C_{12}$) (μg/mL) |
|---|---|---|---|
| | Exponential | Stationary | |
| pBAD34-BTE | 100 ± 9 | 1200 ± 240 | 254 ± 8 (34.3) |
| pBAD34-BTE-H204A | 96 ± 15 | 840 ± 170 | 164 ± 7 (4.9) |
| pBAD18-BTE | 24 ± 3 | 110 ± 10 | 402 ± 28 (68.6) |
| pBAD18-BTE-H204A | 24 ± 2 | 70 ± 8 | 133 ± 1 (2.0) |
| pBAD33-BTE | 5 ± 1 | 19 ± 2 | 540 ± 2 (77.0) |
| pBAD33-BTE-H204A | 7 ± 1 | 13 ± 3 | 131 ± 14 (2.0) |
| pBAD35-BTE | 3 ± 0 | 5 ± 0 | 481 ± 3 (69.6) |
| pBAD35-BTE-H204A | 4 ± 0 | 2 ± 0 | 133 ± 2 (1.6) |
| chromosome (fadD::BTE) | ~1** | ~1** | 195 ± 12 (21.4) |
| chromosome (fadD::BTE-H204A) | ~1** | ~1** | 131 ± 15 (1.7) |

*Culture samples were harvested during early exponential phase ($OD_{600}$ of approximately 0.2) immediately prior to induction and during early stationary phase (7.7 h after inoculation). Errors are propagated standard deviations about the mean of three replicate samples.
**Not experimentally verified.

To determine whether copy number correlated with fatty acid production, total fatty acids were extracted and derivatized for analysis by GC/MS after 23 hours (FIG. 4 and Table 4). In strains expressing functional BTE, the predominant fatty acid chain length shifted dramatically from $C_{16}$ to $C_{12}$, with $C_{12}$ fatty acids accounting for up to 75 percent of the total fatty acid composition. For the culture expressing pBAD33-BTE, approximately 15 percent of $C_{12}$ and 59 percent of $C_{14}$ fatty acids were unsaturated. Lower but significant levels of hydroxylated $C_{12}$, an intermediate in the fatty acid elongation cycle, were also observed but not quantified in functional BTE expressing strains.

As shown in FIG. 4 and Table 4, the strain with the chromosomal BTE insertion accumulated the lowest fatty acid titer (0.195±0.01 g/L) of all the BTE-expressing strains. Of the functional BTE-expressing plasmids, the lowest titer (0.25±0.01 g/L) was observed from the highest copy number plasmid, pBAD34-BTE. The plasmid with the lower of the two intermediate overall copy numbers, pBAD33-BTE, accumulated the highest titer of fatty acids (0.54±0.00 g/L). The plasmids with copy numbers just above and below that of pBAD33-BTE (pBAD35-BTE and pBAD18-BTE, respectively) accumulated a slightly lower titer of fatty acids (0.48±0.00 g/L and 0.40±0.03 g/L, respectively). Strains harboring a non-functional BTE gene on the various plasmids accumulated similar quantities of predominantly $C_{16}$ fatty acids, as expected. These data show that expression of BTE from a plasmid having an intermediate copy number results in the highest fatty acid production.

An appropriate level of thioesterase expression can also be achieved by altering the amount of inducer present in the media, such as when expressed on a higher-copy plasmid and/or expressed from a stronger promoter. Here we show data obtained for a strain harboring pTRC99A plasmids containing a DNA cassette consisting of the TRC promoter, a consensus ribosome binding site, and the optimized, active *Umbellularia californica* thioesterase (pTRC99A-BTE) or the inactive mutant (pTRC99A-BTE-H204A). In addition to being a higher-copy plasmid, the pTRC99A plasmid contains the TRC promoter. The TRC promoter is an extremely strong promoter, capable of expressing protein to a level of about 15-30% total cell protein. The fluorescence of the cultures mixed with Nile red, a fluorescent dye, is proportional to the hydrophobicity (fatty acid content) of its environment.

Figure 5:
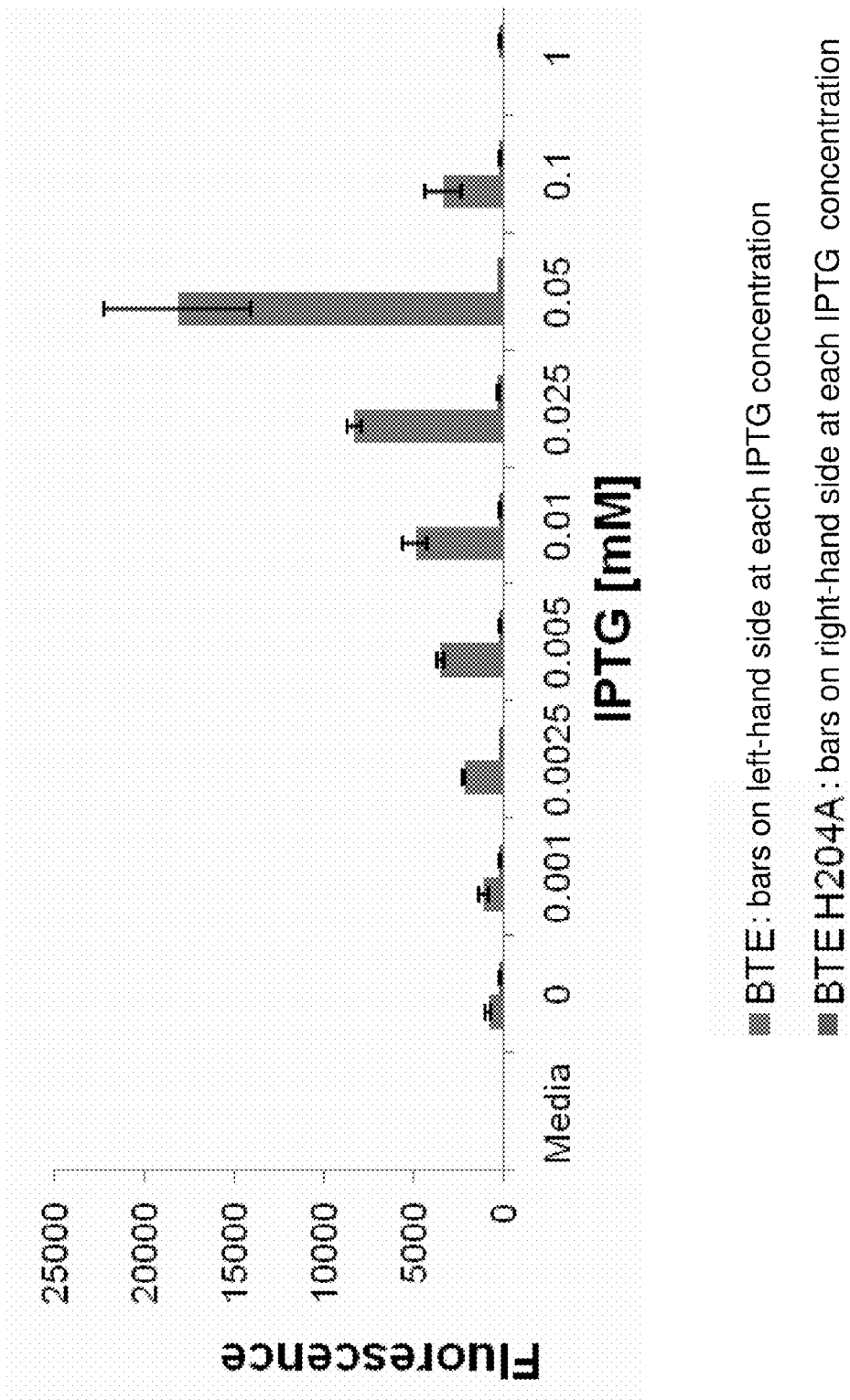
FIG. 5 depicts a plot of Nile red fluorescence as a function of inducer (IPTG) concentration for cultures of *E. coli* harboring pTRC99A plasmids containing a DNA cassette consisting of the TRC promoter, a consensus ribosome binding site, and the optimized, active *Umbellularia californica* thioesterase (pTRC99A-BTE) or the inactive mutant (pTRC99A-BTE-H204A).

Shown in FIG. 5 is a plot of the Nile red fluorescence as a function of inducer (IPTG) concentration for cultures of *E. coli* harboring plasmids with the active *Umbellularia californica* thioesterase (BTE) or the inactive mutant (BTE-H204A). Users familiar with the art will use 1 mM IPTG to achieve maximal transcription from this promoter system. The plot in FIG. 5 shows that a submaximal concentration of IPTG (~50 μM) maximizes the fluorescence.

A strain carrying a $P^{lacI}$-lacI-$P^{TRC}$-BTE-term$^{rrnb}$ cassette in place of the chromosomal fadD gene was constructed. Full induction with 1 mM IPTG resulted in one-third of the fatty acid titer observed compared to induction with 50 μM IPTG (i.e., the optimal induction level in the corresponding plasmid based system). We have subsequently integrated additional copies of the BTE cassette in two other β-oxidation genes to obtain higher titers. These include the fadBA operon (containing fadB and fadA) and fadE.

It can be concluded that expression of BTE on an intermediate copy plasmid or inducing expression of BTE at submaximal levels from a higher-copy plasmid results in the highest level of fatty acid production. Without being limited by mechanism, one possible explanation for the lower fatty acid production with higher copy number plasmids is that higher quantities of functional thioesterase are produced from such plasmids, resulting in an initially rapid rate of accumulation of medium-chain free fatty acids. As there is no known protein-mediated export mechanism for free fatty acids, they likely pass across the inner membrane via a transmembrane flip (Black et. al., (2003)*Microbiol. Mol. Biol. Rev.* 67:454-472). Dodecanoic acid, the dominant BTE product, has a much higher water solubility than longer chain fatty acids (Vorum et al., (1992) *Biochim. Biophys. Acta.* 1126:135-142) and can possibly cross the outer membrane through porins (Hearn et al., (2009) *Nature* 458:367-370). Too rapid an accumulation of $C_{12}$ and $C_{14}$ free fatty acids in the inner membrane may disrupt the membrane integrity and result in cell lysis. A second possible explanation is that higher quantities of functional thioesterase significantly deplete $C_{12}$ and $C_{14}$ acyl-ACPs destined for membrane phospholipid incorporation, resulting in a reduced number of viable cells.

Figure 6:
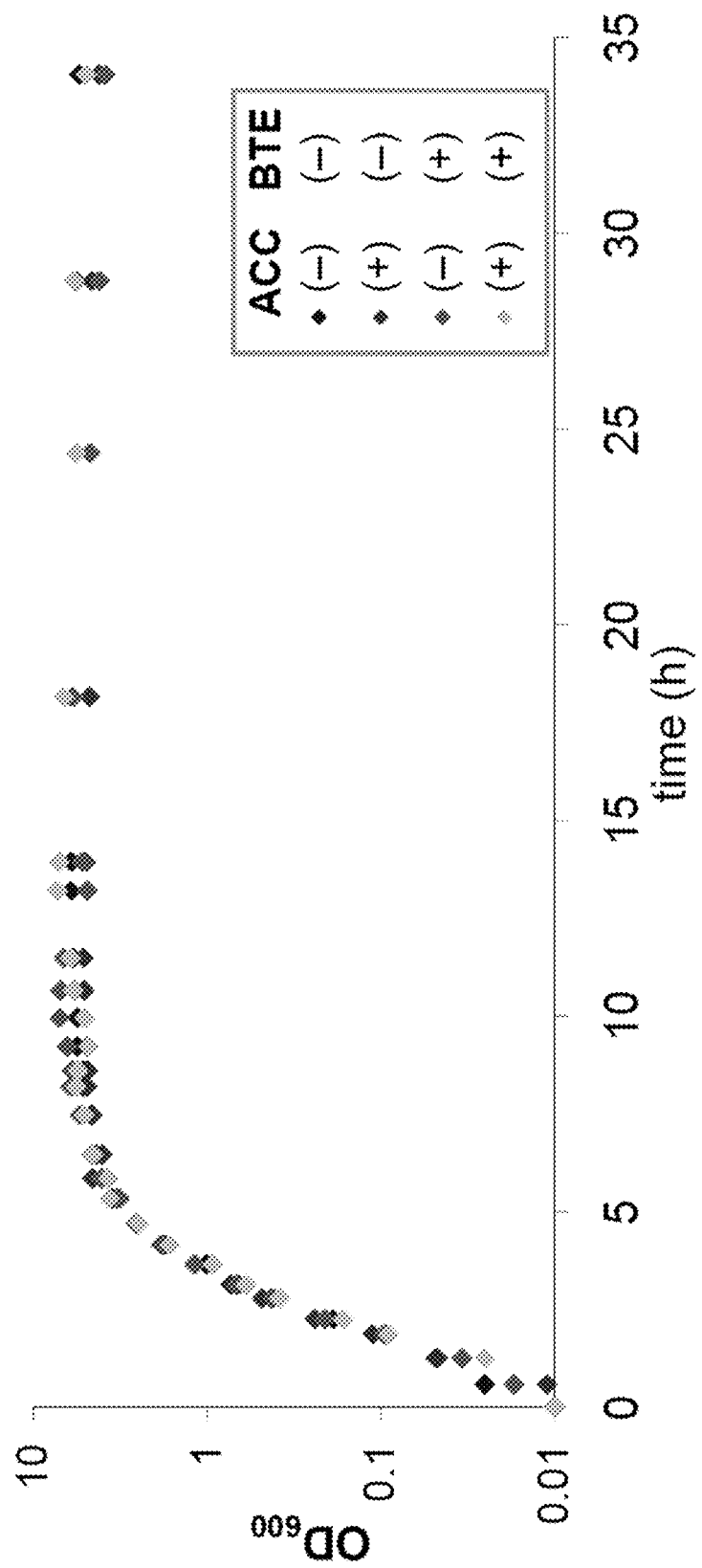
FIG. 6 depicts a growth curve in $OD_{600}$ as a function of time for *E. coli* strain RL08 harboring combinations of plasmids pBAD35-BTE or pBAD35-BTE-H204A and pBAD33-ACC or pBAD33 grown at 37° C. in LB medium supplemented with 0.4% (v/v) glycerol, 25 µg/mL of kanamycin, and 34 µg/mL of chloramphenicol. Growth rates were similar for all strains.

Co-overexpression of Acetyl-CoA Carboxylase: The conversion of acetyl-CoA to malonyl-CoA by acetyl-CoA carboxylase (ACC) has been identified as a rate-limiting step in fatty acid biosynthesis (Davis et. al, 2000). To see if higher production could be achieved over expression of BTE alone, the four subunits of acetyl-CoA carboxylase (ACC) were cloned as an artificial operon (accDABC) on a low-intermediate copy arabinose-inducible plasmid to yield pBAD33-ACC. To co-express BTE, pBAD35-BTE was selected due to its compatibility with pBAD33-ACC and its relatively high level of fatty acid overproduction. Four cultures of *E. coli* strain RL08 harboring combinations of either pBAD33 or pBAD33-ACC, and pBAD35-BTE or pBAD35-BTE-H204A, were grown in shake flasks in 500 mL of LB medium supplemented with 0.4% (v/v) glycerol as a carbon source. As shown in FIG. 6, all four cultures displayed similar growth rates.

Figure 7:
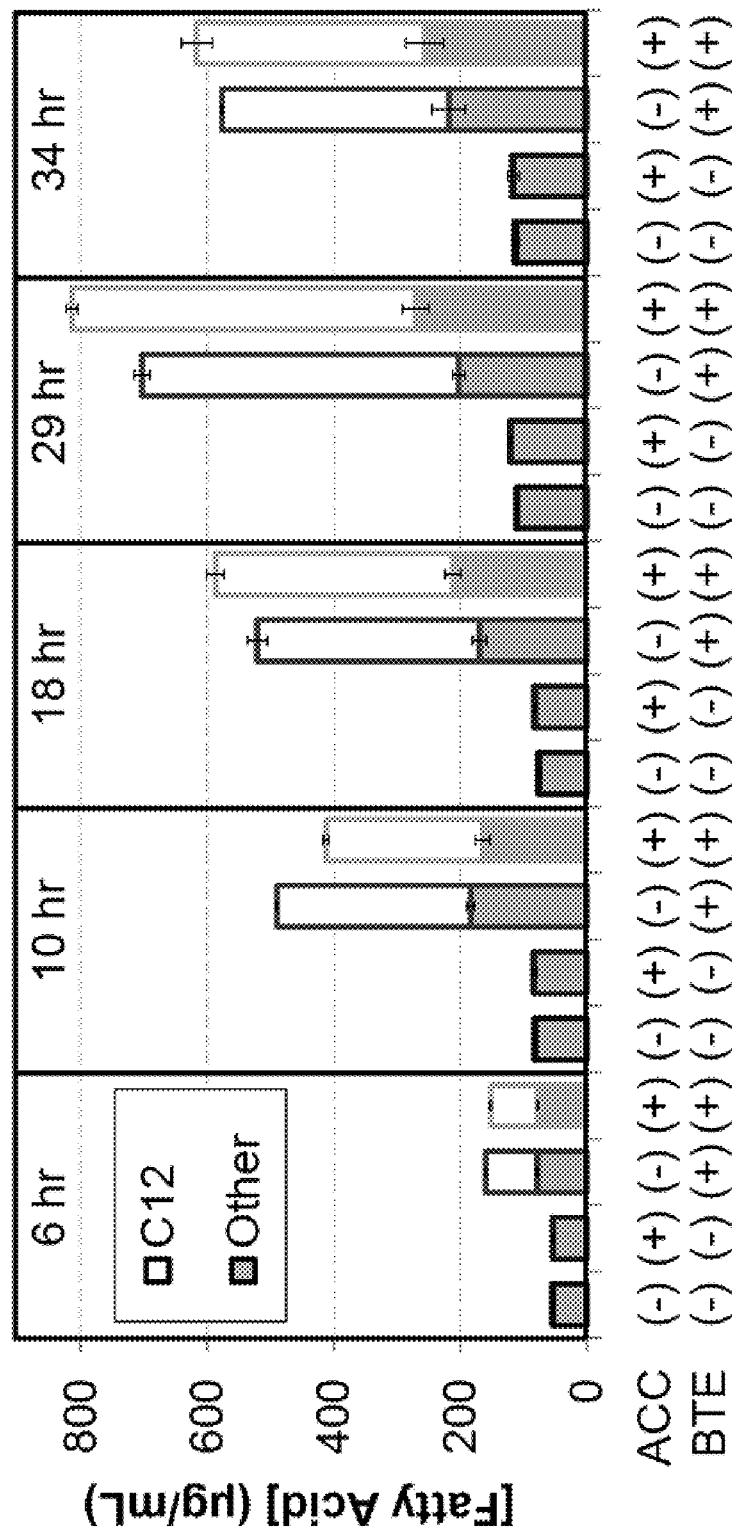
FIG. 7 depicts total and $C_{12}$ fatty acid production for *E. coli* strain RL08 harboring combinations of plasmids pBAD35-BTE or pBAD35-BTE-H204A and pBAD33-ACC or pBAD33 grown at 37° C. in LB medium supplemented with 0.4% (v/v) glycerol, 25 µg/mL of kanamycin, and 34 µg/mL of chloramphenicol. Shown are total (filled bars) and $C_{12}$ chain length (saturated and estimated unsaturated, open bars) of fatty acid titers (µg/mL culture medium) for selected times during cell growth as indicated (6, 10, 18, 29, and 34 h). Error bars represent standard deviations about the mean for three replicate samples for either $C_{12}$ fatty acids (upper bars) of total fatty acids including $C_{12}$ (lower bars).
Figure 8:
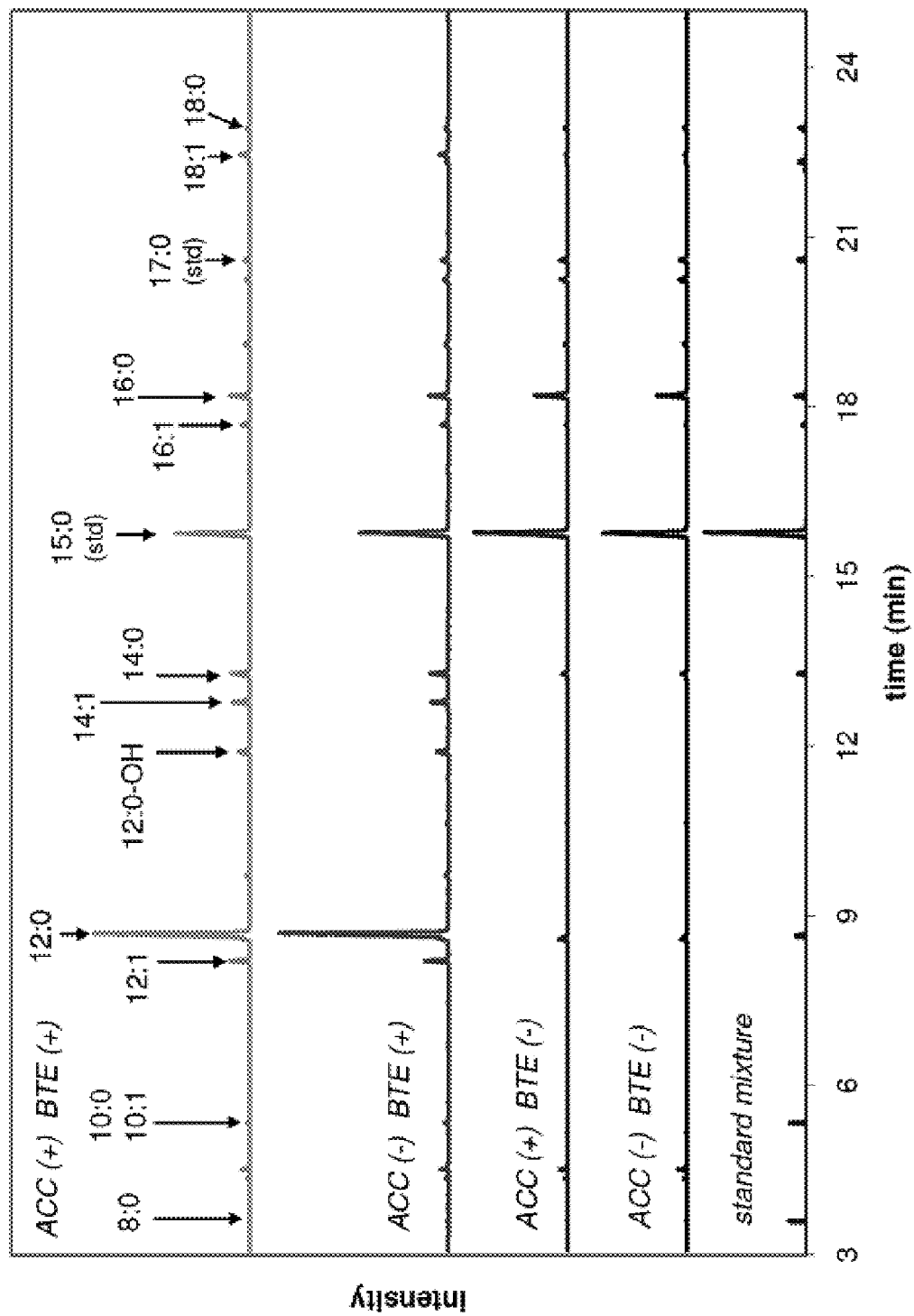
FIG. 8 depicts representative chromatograms (from 34-hour samples, undiluted hexane extracts) of BTE- and/or ACC-expressing *E. coli* strains and a control *E. coli* strain, with quantified peaks indicated. Very large increases in the levels of $C_{12}$ and $C_{14}$ species are clearly observed in BTE-expressing cultures. Labeled peaks that are not present in the standard mixture (10:1, 12:1, 12:0-OH, and 14:1) were identified by comparing their mass spectra to the National Institute of Standards and Technology (NIST) library.

Fatty acids were extracted and derivatized for analysis by GC/MS at several times (FIG. 7; see FIG. 8 for the various fatty acid species produced). Elevated levels of fatty acids were detected at the onset of stationary phase in cultures expressing BTE (e.g., at about 10 hours; see FIGS. 3 and 4). Fatty acid levels were maximal between 24 and 34 hours, with maximum accumulation observed at approximately 28 hours post-inoculation. Specifically, at 28.8 hours, a 7-fold increase in total fatty acids was measured in cells harboring pBAD33-ACC and pBAD35-BTE versus the negative control. The increase was primarily in $C_{12}$ fatty acids. Over the course of growth, the predominant fatty acid chain length shifted dramatically from $C_{16}$ to $C_{12}$, with $C_{12}$ fatty acids representing over 66 percent of the total fatty acid composition. Both saturated and unsaturated species of the $C_{12}$ fatty acids were present. Approximately 10 percent of $C_{12}$ and 52 percent of $C_{14}$ fatty acids were unsaturated. Lower but significant levels of hydroxylated $C_{12}$, an intermediate in the fatty acid elongation cycle, were also observed but not quantified. The strain expressing both BTE and overexpressing ACC (pBAD35-BTE and pBAD33-ACC) exhibited a modest increase in fatty acid titer (0.81±0.02 g/L) relative to a strain expressing BTE alone (pBAD35-BTE and pBAD33) (0.70±0.01 g/L). This modest increase leads to significant increases in fatty acid production when scaled-up on an industrial level.

Microarray data suggests that expression of BTE alone dramatically increases gene expression of the four subunits of ACC, possibly by an uncharacterized transcriptional activation mechanism, which may explain the modest effect. Microarray experiments were performed to identify changes in gene expression that result from expression of the BTE *U. californica* thioesterase (pBAD35-BTE) with or without the overexpression of accDABC (pBAD33-ACC). The BTE-H204A non-functional thioesterase (pBAD35-BTE-H204A) and empty vector (pBAD33) were used as controls. mRNA was isolated in exponential and stationary phase from cultures grown in M9-minimal media supplemented with glycerol as a carbon source. cDNA was synthesized and hybridized to custom microarrays (NimbleGen, Madison, Wis.) representing the open reading frames of *E. coli* MG1655. Data was analyzed in Arraystar software (DNAstar, Madison, Wis.).

Table 5 shows the fold change in mRNA levels from strains harboring combinations of BTE and/or accDABC versus strains harboring the BTE-H204A and empty vector controls. The accA, accB, accC, and accD ACC subunits constituted the top four differentially expressed genes in each of the strains shown. This includes the strains not ectopically expressing accDABC. This data suggests that expression of BTE alone upregulates expression of the genes of the four ACC subunits. These results are in agreement with a previous observation by Ohlrogge et al. (1995), wherein expression of BTE in *E. coli* increases the levels of biotin carboxyl carrier protein (AccB). The expression levels of AccA, AccC, and AccD were not quantified in this prior work. Additionally, heterologous expression of BTE in the seeds of the rapeseed plant, *Brassica napus* was shown to increase expression levels of its native biotin carboxyl carrier protein and biotin carboxylase (Eccleston et. al., (1998) *Plant Cell* 10:613-621). Plants and bacteria both have similar multi-subunit acetyl-CoA carboxylases (Cronan et. al., (2002) *Prog. Lipid. Res.* 41:407-435). The strain expressing only ACC does not overproduce fatty acids, as previously observed (Davis et. al., 2001).

TABLE 5

Fold change* of top four differentially expressed genes resulting from ectopic expression of BTE and/or ACC.

| | Exponential Phase | | Stationary Phase | |
|---|---|---|---|---|
| | Cond 1: BTE, ACC Cond 2: BTE-H204A, pBad33 | | Cond 1: BTE, ACC Cond 2: BTE-H204A, pBad33 | |
| Effect of BTE expression | accA | 28.8 | accC | 365.5 |
| | accC | 21.0 | accA | 64.0 |

TABLE 5-continued

Fold change* of top four differentially expressed genes resulting from ectopic expression of BTE and/or ACC.

|  |  | Exponential Phase |  | Stationary Phase |
|---|---|---|---|---|
| with ACC overexpression | accD accB | 14.6 13.1 | accB accD | 62.5 29.2 |
|  |  | Cond 1: BTE, pBad33 Cond 2: BTE-H204A, pBad33 |  | Cond 1: BTE, pBad33 Cond 2: BTE-H204A, pBad33 |
| Effect of BTE expression alone | accA accC accD accB | 27.2 21.7 14.3 12.2 | accC accA accB accD | 383.8 70.7 64.9 30.3 |

*Fold change is mRNA Condition 1/mRNA Condition 2.

Extraction and Conversion of Fatty Acids to Alkanes: To demonstrate a complete process for fuel production, fatty acids were extracted from approximately 400 mL of the overproducing culture (the remaining volume from an original culture volume of 500 mL) overexpres sing both ACC and BTE at 34 hours, with a total measured saturated and unsaturated $C_{12}$ fatty acid titer of 0.36±0.02 g/L. Decane was selected to facilitate analysis of the dominant undecane product, due to the presence of significant undecane impurities in other commercially available alkanes of higher molecular weight, such as tridecane. While decane is mildly toxic to microbes (Sardessai et. al., (2002) *Res. Microbiol.* 153:263-268), larger alkanes such as dodecane are essentially non-toxic and their use to extract metabolites during cell growth has been previously demonstrated (Janikowski et al., (2002) *Appl. Microbiol. Biotechnol.* 59:368-376; Newman et al., (2006) *Biotechnol. Bioeng.* 95:684-691). The emulsion resulting from decane addition was acidified and centrifuged to facilitate phase separation, and the decane layer was collected. Approximately 60 percent of the decane added could be collected as a de-emulsified liquid layer.

Fatty acids in the decane extractions were decarboxylated at 100 percent conversion in the presence of hydrogen over a 1 weight percent Pd/C catalyst in a plug flow reactor operating at 300° C. and 12 bar. The catalytic decarboxylation of fatty acids over Pd/C catalysts has previously been demonstrated using a semi-batch reactor operating at 300° C. (Mäki-Arvela et al., (2007) *Energy Fuels* 21:30-41). Under these conditions unsaturated fatty acids are fully hydrogenated, which is desirable for stability of the product during storage. In the collected alkane product, 0.44±0.3 g/L (culture volume) undecane was obtained, representing a complete recovery and conversion of $C_{12}$ fatty acids from the culture medium. Smaller amounts of tridecane and pentadecane were also present, as expected from the fatty acid composition.

The extraction method described above can be used in an industrial process in which a desired hydrocarbon product is used to both extract fatty acids from a fermentor as well as act as the solvent for the decarboxylation reaction (FIG. 9). A product stream is continuously or semi-continuously collected at a rate that matches the fatty acid production rate, with the remainder of the alkane phase recycled as an extractant.

Conclusion: A strain of *E. coli* that exhibits an approximately seven-fold increase in fatty acid production (predominantly $C_{12}$ fatty acids) over the baseline strain (RL08) was metabolically engineered. One aspect of the strategy was utilizing an intermediate copy number vector or low induction for expression of BTE. The successful conversion of overproduced fatty acids to a useful enriched liquid alkane stream was demonstrated by a novel process that couples microbial production of free fatty acids to a catalytic reaction step. The invention includes any other genetic and process improvements to increase fatty acid yields and alkane recovery in addition to those disclosed herein.

What is claimed is:

1. An isolated host cell for producing a fatty acid product comprising an exogenous nucleic acid encoding a thioesterase (EC 3.1.2.14), wherein:
   the thioesterase comprises a sequence at least 80% identical to SEQ ID NO:2;
   the host includes no more than 250 copies of the nucleic acid;
   an acyl-CoA synthetase (EC 6.2.1.3) in the host is functionally deleted; and
   the host is recombinantly stable at 37° C.

2. The host of claim 1 wherein the host is growth-competent at 37° C.

3. The host of claim 1 wherein the nucleic acid is operably connected to an origin of replication obtained from a plasmid selected from the group consisting of pBR322, pACYC, pBBR1, and pSC101.

4. The host of claim 1 wherein the host includes no more than 30 copies of the nucleic acid.

5. The host of claim 1 wherein the host includes of from 2 to 250 copies of the nucleic acid.

6. The host of claim 1 wherein the host includes of from 5 to 100 copies of the nucleic acid.

7. The host of claim 1 wherein the host includes of from 5 to 30 copies of the nucleic acid.

8. The host of claim 1 wherein the exogenous nucleic acid is codon optimized.

9. The host of claim 1 wherein the exogenous nucleic acid is a nucleic acid sequence comprising SEQ ID NO:1.

10. The host of claim 1 wherein the thioesterase is obtained from *Umbellularia californica*.

11. The host of claim 1 further comprising an exogenous nucleic acid encoding an acetyl-CoA carboxylase (EC 6.4.1.2).

12. The host of claim 11 wherein the nucleic acid encoding the acetyl-CoA carboxylase includes an artificial operon comprising accA, accB, accC, and accD from *E. coli*.

13. A method for producing a fatty acid product comprising culturing an isolated host as recited in claim 1 at 37° C., wherein the host overproduces the fatty acid product.

14. The method of claim 13 further comprising maintaining the nucleic acid in the host at a copy number of 30 copies or fewer.

15. The method of claim 13 comprising maintaining the nucleic acid in the host at a copy number of from 10 to 30.

16. The method of claim 13 wherein the nucleic acid is operably connected to an inducible promoter, and wherein the method further comprises culturing the host in presence of a sub-saturating amount of an effector of the inducible promoter.

17. The method of claim 13 wherein the nucleic acid is operably connected to a repressible promoter, and wherein the method further comprises culturing the host in presence of a repressor of the repressible promoter.

18. The method of claim 13 further comprising:
maintaining the nucleic acid in the host at a copy number of 50 copies or more; and
culturing the host in presence of a sub-saturating amount of an effector of an inducible promoter operably connected to the nucleic acid, or
culturing the host in presence of a repressor of a repressible promoter operably connected to the nucleic acid.

19. The method of claim 13 wherein the cultured host further comprises an exogenous nucleic acid encoding an acetyl-CoA carboxylase (EC 6.4.1.2).

20. The host of claim 1 wherein the host is a microorganism, and the thioesterase is a thioesterase comprising a sequence at least 80% identical to SEQ ID NO:2.

21. The host of claim 1 wherein the host is a microorganism, the thioesterase is a thioesterase comprising a sequence at least 80% identical to SEQ ID NO:2, and the acyl-CoA synthetase is a microbial acyl-CoA synthetase.

22. The host of claim 21 wherein the host is a bacterium or a yeast.

23. The host of claim 22 wherein the thioesterase is a thioesterase comprising a sequence at least 90% identical to SEQ ID NO:2.

24. The host of claim 1 wherein the host is an isolated host cell, the host is a bacterium or a yeast, the thioesterase is a thioesterase comprising a sequence at least 80% identical to SEQ ID NO:2, and the acyl-CoA synthetase is a FadD acyl-CoA synthetase or an FAA acyl-CoA synthetase.

25. The host of claim 1 wherein the host is an isolated host cell, the host is a bacterium or a yeast, the thioesterase is a thioesterase comprising a sequence at least 90% identical to SEQ ID NO:2, and the acyl-CoA synthetase is a FadD acyl-CoA synthetase or an FAA acyl-CoA synthetase.

* * * * *

SEQUENCE LISTING

<160> NUMBER OF SEQ ID NOS: 29

<210> SEQ ID NO 1
<211> LENGTH: 930
<212> TYPE: DNA
<213> ORGANISM: Umbellularia californica
<220> FEATURE:
<221> NAME/KEY: CDS
<222> LOCATION: (21)..(923)

<400> SEQUENCE: 1

```
cccgggagga ggattataaa atg act cta gag tgg aaa ccg aaa cca aaa ctg       53
                     Met Thr Leu Glu Trp Lys Pro Lys Pro Lys Leu
                      1               5                  10 cct caa ctg ctg gat gat cac ttc ggt ctg cac ggt ctg gtg ttt cgt      101
Pro Gln Leu Leu Asp Asp His Phe Gly Leu His Gly Leu Val Phe Arg
             15                  20                  25 cgt act ttc gca att cgt tct tat gaa gtg ggt cca gat cgt tct acc      149
Arg Thr Phe Ala Ile Arg Ser Tyr Glu Val Gly Pro Asp Arg Ser Thr
         30                  35                  40 tcc atc ctg gcc gtc atg aac cac atg cag gaa gcc acc ctg aat cac      197
Ser Ile Leu Ala Val Met Asn His Met Gln Glu Ala Thr Leu Asn His
     45                  50                  55 gcg aaa tct gtt ggt atc ctg ggt gat ggt ttc ggc act act ctg gaa      245
Ala Lys Ser Val Gly Ile Leu Gly Asp Gly Phe Gly Thr Thr Leu Glu
60                  65                  70                  75
```

```
atg tct aaa cgt gac ctg atg tgg gta gtg cgt cgc acc cac gta gca    293
Met Ser Lys Arg Asp Leu Met Trp Val Val Arg Arg Thr His Val Ala
            80                  85                  90 gta gag cgc tac cct act tgg ggt gac act gtg gaa gtc gag tgt tgg    341
Val Glu Arg Tyr Pro Thr Trp Gly Asp Thr Val Glu Val Glu Cys Trp
        95                 100                 105 att ggc gcg tcc ggt aac aat ggt atg cgt cgc gat ttt ctg gtc cgt    389
Ile Gly Ala Ser Gly Asn Asn Gly Met Arg Arg Asp Phe Leu Val Arg
            110                 115                 120 gac tgt aaa acg ggc gaa atc ctg acg cgt tgc acc tcc ctg agc gtt    437
Asp Cys Lys Thr Gly Glu Ile Leu Thr Arg Cys Thr Ser Leu Ser Val
        125                 130                 135 ctg atg aac acc cgc act cgt cgc ctg tct acc atc ccg gac gaa gtg    485
Leu Met Asn Thr Arg Thr Arg Arg Leu Ser Thr Ile Pro Asp Glu Val
140                 145                 150                 155 cgc ggt gag atc ggt cct gct ttc atc gat aac gtg gca gtt aaa gac    533
Arg Gly Glu Ile Gly Pro Ala Phe Ile Asp Asn Val Ala Val Lys Asp
            160                 165                 170 gac gaa atc aag aaa ctg caa aaa ctg aac gac tcc acc gcg gac tac    581
Asp Glu Ile Lys Lys Leu Gln Lys Leu Asn Asp Ser Thr Ala Asp Tyr
        175                 180                 185 atc cag ggc ggt ctg act ccg cgc tgg aac gac ctg gat gtt aat cag    629
Ile Gln Gly Gly Leu Thr Pro Arg Trp Asn Asp Leu Asp Val Asn Gln
            190                 195                 200 cat gtg aac aac ctg aaa tac gtt gct tgg gtc ttc gag act gtg ccg    677
His Val Asn Asn Leu Lys Tyr Val Ala Trp Val Phe Glu Thr Val Pro
        205                 210                 215 gac agc att ttc gaa agc cat cac att tcc tct ttt act ctg gag tac    725
Asp Ser Ile Phe Glu Ser His His Ile Ser Ser Phe Thr Leu Glu Tyr
220                 225                 230                 235 cgt cgc gaa tgt act cgc gac tcc gtt ctg cgc agc ctg acc acc gta    773
Arg Arg Glu Cys Thr Arg Asp Ser Val Leu Arg Ser Leu Thr Thr Val
            240                 245                 250 agc ggc ggt tct agc gag gca ggt ctg gtc tgc gac cat ctg ctg caa    821
Ser Gly Gly Ser Ser Glu Ala Gly Leu Val Cys Asp His Leu Leu Gln
        255                 260                 265 ctg gaa ggc ggc tcc gaa gtc ctg cgt gcg cgt acg gag tgg cgt cca    869
Leu Glu Gly Gly Ser Glu Val Leu Arg Ala Arg Thr Glu Trp Arg Pro
            270                 275                 280 aag ctg acg gat tct ttc cgc ggc atc tcc gta att ccg gcg gaa cct    917
Lys Leu Thr Asp Ser Phe Arg Gly Ile Ser Val Ile Pro Ala Glu Pro
        285                 290                 295 cgt gtt taagctt                                                    930
Arg Val
300

<210> SEQ ID NO 2
<211> LENGTH: 301
<212> TYPE: PRT
<213> ORGANISM: Umbellularia californica

<400> SEQUENCE: 2

Met Thr Leu Glu Trp Lys Pro Lys Pro Lys Leu Pro Gln Leu Leu Asp
1               5                   10                  15

Asp His Phe Gly Leu His Gly Leu Val Phe Arg Arg Thr Phe Ala Ile
            20                  25                  30

Arg Ser Tyr Glu Val Gly Pro Asp Arg Ser Thr Ser Ile Leu Ala Val
        35                  40                  45

Met Asn His Met Gln Glu Ala Thr Leu Asn His Ala Lys Ser Val Gly
    50                  55                  60
```

```
Ile Leu Gly Asp Gly Phe Gly Thr Thr Leu Glu Met Ser Lys Arg Asp
 65                  70                  75                  80

Leu Met Trp Val Val Arg Arg Thr His Val Ala Val Glu Arg Tyr Pro
                 85                  90                  95

Thr Trp Gly Asp Thr Val Glu Val Glu Cys Trp Ile Gly Ala Ser Gly
            100                 105                 110

Asn Asn Gly Met Arg Arg Asp Phe Leu Val Arg Asp Cys Lys Thr Gly
        115                 120                 125

Glu Ile Leu Thr Arg Cys Thr Ser Leu Ser Val Leu Met Asn Thr Arg
    130                 135                 140

Thr Arg Arg Leu Ser Thr Ile Pro Asp Glu Val Arg Gly Glu Ile Gly
145                 150                 155                 160

Pro Ala Phe Ile Asp Asn Val Ala Val Lys Asp Glu Ile Lys Lys
                165                 170                 175

Leu Gln Lys Leu Asn Asp Ser Thr Ala Asp Tyr Ile Gln Gly Gly Leu
            180                 185                 190

Thr Pro Arg Trp Asn Asp Leu Asp Val Asn Gln His Val Asn Asn Leu
        195                 200                 205

Lys Tyr Val Ala Trp Val Phe Glu Thr Val Pro Asp Ser Ile Phe Glu
    210                 215                 220

Ser His His Ile Ser Ser Phe Thr Leu Glu Tyr Arg Arg Glu Cys Thr
225                 230                 235                 240

Arg Asp Ser Val Leu Arg Ser Leu Thr Thr Val Ser Gly Gly Ser Ser
                245                 250                 255

Glu Ala Gly Leu Val Cys Asp His Leu Leu Gln Leu Glu Gly Gly Ser
            260                 265                 270

Glu Val Leu Arg Ala Arg Thr Glu Trp Arg Pro Lys Leu Thr Asp Ser
        275                 280                 285

Phe Arg Gly Ile Ser Val Ile Pro Ala Glu Pro Arg Val
    290                 295                 300

<210> SEQ ID NO 3
<211> LENGTH: 60
<212> TYPE: DNA
<213> ORGANISM: Artificial Sequence
<220> FEATURE:
<223> OTHER INFORMATION: fadDKO_fwd

<400> SEQUENCE: 3
ggttgcgatg acgacgaaca cgcattttag aggtgaagaa gtgtaggctg gagctgcttc      60

<210> SEQ ID NO 4
<211> LENGTH: 60
<212> TYPE: DNA
<213> ORGANISM: Artificial Sequence
<220> FEATURE:
<223> OTHER INFORMATION: fadDKO_rev

<400> SEQUENCE: 4
cgccggatta accggcgtct gacgactgac ttaacgctca attccgggga tccgtcgacc      60

<210> SEQ ID NO 5
<211> LENGTH: 21
<212> TYPE: DNA
<213> ORGANISM: Artificial Sequence
<220> FEATURE:
<223> OTHER INFORMATION: fadDKO_colPCR_fwd

<400> SEQUENCE: 5
```

-continued

```
acggcatgta tatcatttgg g                                           21

<210> SEQ ID NO 6
<211> LENGTH: 23
<212> TYPE: DNA
<213> ORGANISM: Artificial Sequence
<220> FEATURE:
<223> OTHER INFORMATION: fadDKO_colPCR_rev

<400> SEQUENCE: 6
ctttagtggg cgtcaaaaaa aac                                         23

<210> SEQ ID NO 7
<211> LENGTH: 21
<212> TYPE: DNA
<213> ORGANISM: Artificial Sequence
<220> FEATURE:
<223> OTHER INFORMATION: araBADKO_colPCR_fwd

<400> SEQUENCE: 7
aagcgggacc aaagccatga c                                           21

<210> SEQ ID NO 8
<211> LENGTH: 21
<212> TYPE: DNA
<213> ORGANISM: Artificial Sequence
<220> FEATURE:
<223> OTHER INFORMATION: araBADKO_colPCR_rev

<400> SEQUENCE: 8
aggagacttc tgtcccttgc g                                           21

<210> SEQ ID NO 9
<211> LENGTH: 34
<212> TYPE: DNA
<213> ORGANISM: Artificial Sequence
<220> FEATURE:
<223> OTHER INFORMATION: accD_fwd

<400> SEQUENCE: 9
cccgagctca ggtccctaat gagctggatt gaac                             34

<210> SEQ ID NO 10
<211> LENGTH: 31
<212> TYPE: DNA
<213> ORGANISM: Artificial Sequence
<220> FEATURE:
<223> OTHER INFORMATION: accD_rev

<400> SEQUENCE: 10 cccccccgggt caggcctcag gttcctgatc c                               31

<210> SEQ ID NO 11
<211> LENGTH: 37
<212> TYPE: DNA
<213> ORGANISM: Artificial Sequence
<220> FEATURE:
<223> OTHER INFORMATION: accA_fwd

<400> SEQUENCE: 11
gggcccggga ggaatactat gagtctgaat ttccttg                          37

<210> SEQ ID NO 12
<211> LENGTH: 38
<212> TYPE: DNA
<213> ORGANISM: Artificial Sequence
<220> FEATURE:
```

<223> OTHER INFORMATION: accA_rev

<400> SEQUENCE: 12
ggggtcgacc tcgagtttac gcgtaaccgt agctcatc           38

<210> SEQ ID NO 13
<211> LENGTH: 32
<212> TYPE: DNA
<213> ORGANISM: Artificial Sequence
<220> FEATURE:
<223> OTHER INFORMATION: accBC_fwd

<400> SEQUENCE: 13
cccctcgaga cggaacccac tcatggatat tc                 32

<210> SEQ ID NO 14
<211> LENGTH: 37
<212> TYPE: DNA
<213> ORGANISM: Artificial Sequence
<220> FEATURE:
<223> OTHER INFORMATION: accBC_rev

<400> SEQUENCE: 14
cccgcatgct tattttcct gaagaccgag ttttttc             37

<210> SEQ ID NO 15
<211> LENGTH: 16
<212> TYPE: DNA
<213> ORGANISM: Artificial Sequence
<220> FEATURE:
<223> OTHER INFORMATION: BTE-H204A_mega_rev

<400> SEQUENCE: 15
tctcatccgc caaaac                                   16

<210> SEQ ID NO 16
<211> LENGTH: 32
<212> TYPE: DNA
<213> ORGANISM: Artificial Sequence
<220> FEATURE:
<223> OTHER INFORMATION: BTE-H204A_mega_mut

<400> SEQUENCE: 16
tgttaatcag gctgtgaaca acctgaaata cg                 32

<210> SEQ ID NO 17
<211> LENGTH: 16
<212> TYPE: DNA
<213> ORGANISM: Artificial Sequence
<220> FEATURE:
<223> OTHER INFORMATION: BTE-H204A_mega_fwd

<400> SEQUENCE: 17
ttgggctagc gaattc                                   16

<210> SEQ ID NO 18
<211> LENGTH: 24
<212> TYPE: DNA
<213> ORGANISM: Artificial Sequence
<220> FEATURE:
<223> OTHER INFORMATION: pBAD18-to-pBT_fwd

<400> SEQUENCE: 18
ttatgacaac ttgacggcta catc                          24

<210> SEQ ID NO 19

```
<211> LENGTH: 25
<212> TYPE: DNA
<213> ORGANISM: Artificial Sequence
<220> FEATURE:
<223> OTHER INFORMATION: pBAD18-to-pBT_rev

<400> SEQUENCE: 19
agagtttgta gaaacgcaaa aaggc                                              25

<210> SEQ ID NO 20
<211> LENGTH: 21
<212> TYPE: DNA
<213> ORGANISM: Artificial Sequence
<220> FEATURE:
<223> OTHER INFORMATION: BTE-to-pBAD35_fwd

<400> SEQUENCE: 20
acgcttttta tcgcaactct c                                                  21

<210> SEQ ID NO 21
<211> LENGTH: 28
<212> TYPE: DNA
<213> ORGANISM: Artificial Sequence
<220> FEATURE:
<223> OTHER INFORMATION: BTE-to-pBAD35_rev

<400> SEQUENCE: 21
ggggcatgct taaacacgag gttcgcgc                                           28

<210> SEQ ID NO 22
<211> LENGTH: 33
<212> TYPE: DNA
<213> ORGANISM: Artificial Sequence
<220> FEATURE:
<223> OTHER INFORMATION: pBAD33ara_fwd

<400> SEQUENCE: 22
gggctcgagt tatgacaact tgacggctac atc                                     33

<210> SEQ ID NO 23
<211> LENGTH: 34
<212> TYPE: DNA
<213> ORGANISM: Artificial Sequence
<220> FEATURE:
<223> OTHER INFORMATION: pBAD33ara_rev

<400> SEQUENCE: 23
gggagatcta gagtttgtag aaacgcaaaa aggc                                    34

<210> SEQ ID NO 24
<211> LENGTH: 32
<212> TYPE: DNA
<213> ORGANISM: Artificial Sequence
<220> FEATURE:
<223> OTHER INFORMATION: pUC19ara_fwd

<400> SEQUENCE: 24
gggctcgagg tgcctaatga gtgagctaac tc                                      32

<210> SEQ ID NO 25
<211> LENGTH: 30
<212> TYPE: DNA
<213> ORGANISM: Artificial Sequence
<220> FEATURE:
<223> OTHER INFORMATION: pUC19ara_rev

<400> SEQUENCE: 25
```

```
gggagatctt agttaagcca gccccgacac                                    30

<210> SEQ ID NO 26
<211> LENGTH: 18
<212> TYPE: DNA
<213> ORGANISM: Artificial Sequence
<220> FEATURE:
<223> OTHER INFORMATION: qPCR_BTE_fwd

<400> SEQUENCE: 26
ctgtctacca tcccggac                                                 18

<210> SEQ ID NO 27
<211> LENGTH: 26
<212> TYPE: DNA
<213> ORGANISM: Artificial Sequence
<220> FEATURE:
<223> OTHER INFORMATION: qPCR_BTE_rev

<400> SEQUENCE: 27 tcagttttg cagtttcttg atttcg                                         26

<210> SEQ ID NO 28
<211> LENGTH: 20
<212> TYPE: DNA
<213> ORGANISM: Artificial Sequence
<220> FEATURE:
<223> OTHER INFORMATION: qPCR_ompA_fwd

<400> SEQUENCE: 28
tgttgagtac gcgatcactc                                               20

<210> SEQ ID NO 29
<211> LENGTH: 17
<212> TYPE: DNA
<213> ORGANISM: Artificial Sequence
<220> FEATURE:
<223> OTHER INFORMATION: qPCR_ompA_rev

<400> SEQUENCE: 29
gttgtccgga cgagtgc                                                  17
```